United States Patent
Wong et al.

[11] Patent Number: 6,120,803
[45] Date of Patent: Sep. 19, 2000

[54] PROLONGED RELEASE ACTIVE AGENT DOSAGE FORM ADAPTED FOR GASTRIC RETENTION

[75] Inventors: Patrick S. L. Wong, Burlingame; Liang-Chang Dong, Sunnyvale; David E. Edgren, El Granada; Felix Theeuwes, Los Altos; Phyllis I. Gardner, Stanford; Francisco Jao, San Jose; Jason J. Wan, Palo Alto, all of Calif.

[73] Assignee: ALZA Corporation, Mountain View, Calif.

[21] Appl. No.: 09/131,923

[22] Filed: Aug. 10, 1998

Related U.S. Application Data
[60] Provisional application No. 60/055,475, Aug. 11, 1997.

[51] Int. Cl.[7] .............................. A61K 9/22; A61K 9/26
[52] U.S. Cl. ..................... 424/473; 424/468; 424/469; 424/470; 424/486; 424/488; 514/772.2; 514/772.3; 514/777; 514/778; 514/781; 514/782; 514/784
[58] Field of Search .................. 424/457, 468, 424/469, 473, 474, 484, 486, 487, 488, 470

[56] References Cited

U.S. PATENT DOCUMENTS

| | | | |
|---|---|---|---|
| 3,786,813 | 1/1974 | Michaels | 128/260 |
| 4,207,890 | 6/1980 | Mamajek et al. | 128/223 |
| 4,673,564 | 6/1987 | Kawata et al. | 424/494 |
| 4,767,627 | 8/1988 | Caldwell et al. | 424/426 |
| 4,839,177 | 6/1989 | Colombo et al. | 424/482 |
| 4,851,232 | 7/1989 | Urquhart et al. | 424/469 |
| 4,871,548 | 10/1989 | Edgren et al. | 424/488 |
| 5,007,790 | 4/1991 | Shell | 424/451 |
| 5,413,777 | 5/1995 | Sheth et al. | 424/490 |
| 5,443,843 | 8/1995 | Curatolo et al. | 424/464 |
| 5,534,263 | 7/1996 | Wong et al. | 424/473 |
| 5,576,025 | 11/1996 | Akiyama et al. | 424/501 |
| 5,582,837 | 12/1996 | Shell | 424/451 |

OTHER PUBLICATIONS

R. Cargill, L.J. Caldwell, K. Engle, J.A. Fix, P.A. Porter, and C.R. Gardner, Controlled Gastric Emptying. 1. Effects of Physical Properties on Gastric Residence Times of Nondisintegrating Geometric Shapes in Beagle Dogs, Pharmaceuticl Research, vol. 5, No. 8, (1988) 533–536.

R. Cargill, K. Engle, C. R. Gardner, P. Porter, R. V. Sparer, and J.A. Fix, Controlled Gastric Emptying. II. In Vitro Erosion and Gastric Residence Times of an Erodible Device in Beagle Dogs, Pharmaceutical Research, vol. 6, No. 6, (1989) 506–509.

W.S.W. Shalaby, W. E. Blevins, and K. Park, In vitro and in vivo studies of enzyme–digestible hydrogels for oral drug delivery, J. of Controlled Release, 19 (1992) 131–144.

U. Conte, L. Maggi, P. Colombo, and A. La Manna, Multi–layered hydrophilic matrices as constant release devices (Geomatrix™ Systems), J. of Controlled Release, 26 (1993) 39–47.

S. S. Davis, The Design and Evaluation of Controlled Release Systems for the Gastrointestinal Tract, J. of Controlled Release, 2 (1985) 27–38.

(List continued on next page.)

*Primary Examiner*—James M. Spear
*Attorney, Agent, or Firm*—John A. Dhuey; Steven F. Stone

[57] ABSTRACT

The present invention is directed to an active agent dosage form which is adapted for retention in the stomach and useful for the prolonged delivery of an active agent formulation to a fluid environment of use. The active agent dosage form is a polymer matrix that swells upon contact with the fluids of the stomach. A portion of the polymer matrix is surrounded by a band of insoluble material that prevents the covered portion of the polymer matrix from swelling and provides a segment of the dosage form that is of sufficient rigidity to withstand the contractions of the stomach and delay expulsion of the dosage form from the stomach until substantially all of the active agent has been dispensed.

12 Claims, 6 Drawing Sheets

OTHER PUBLICATIONS

A. J. Coupe, S. S. Davis, D. F. Evans, and I. R. Wilding, Correlation of Gastric Emptying of Nondisintegrating Tablets with Gastrointestinal Motility, Pharmaceutical Research, vol. 8, No. 10 (1991), 1281–1285.

K. T. Evans and G. M. Roberts, The Ability of Patients to Swallow Capsules, J. of Clinical and Hospital Pharmacy 6, (1981) 207–208.

H. M. Richter, Stomach and Duodenum, (1988), An Illulstrated Guide to Gastrointestinal Motility, (Edited by D. Kumar and S. Gustavsson, J. Wiley & Sons, pp. 163–174.

J. E. Devereux, J. M. Newton, M. B. Short, The influence of density on the gastrointestinal transit of pellets, J. Pharm. Pharmacol. (1990) 42: 500–501.

L. D. Lewis, A.S.E. Fowle, S. B. Bittiner, A. Bye, and P.E.T. Isaacs, Human gastrointestinal absorption of acyclovir from tablet duedenal infusion and sipped solution, Br. J. Clin. Pharmac 91986), 21, (459–462).

R. Khosla and S. S. Davis, The effect of tablet size on the gastric emptying of non–disintegrating tablets, Inter. Journal of Pharm., 62 (1990), R9–R11.

S. S. Davis, A. F. Stockwell, M.J. Taylor, J. G. Hardy, D. R. Whalley, C. G. Wilson, H. Bechgaard, and F. N. Christensen, The Effect of Density on the Gastric Emptying of Single– and Multiple–Unit Dosage Forms, Pharmaceutical Research, vol. 3, No. 4, (1986) pp. 208–213.

S. S. Davis, F. Norring–Christensen, R. Khosla, L. C. Feeley, Gastric emptying of large single unit dosage forms, J. Phar. Pharmacol. (1988), 40: 205–207.

H.S. Ch'ng, H. Park, P. Kelley, and J. R. Robinson, Bioadhesive Polymers as Platforms for Oral Controlled Drug Delivery II: Synthesis and Evaluation of Some Swelling, Water–Insoluble Bioadhesive Polymers, J. of Pharmaceutical Sciences, vol. 74, No. 4, Apr. 1985, pp. 399–405.

S.S. Davis, The design and evaluation of controlled release dosage forms for oral delivery, S.T.P. PHarma 3 (5) (1987) 412–417.

I.R. Wilding, A. J. Coupe, and S. S. Davis, The Role of $\gamma$–scintigraphy in oral drug delivery, Advanced Drug Delivery Reviews, 7 (1991) 87–117.

A. A. Deshpande, C. T. Rhodes, N. H. Shah, and A. W. Malick, Controlled–Release Drug Delivery Systems for Prolonged Gastric Residence: An Overview, Drug Development and Industrial Pharmacey, 22 (6) 531–539 91996) 1996.

A. A. Deshpande, N. H. Shah, C. T. Rhodes, and W. Malick, Development of a Novel Controlled–Release System for Gastric Retention, Pharm. Research. vol. 14, No. 6, (1997), pp. 815–819.

C. G. Wilson, N. Washington, J. G. Hardy, and S. W. Bond, the influence of food on the absorption of acyclovir: a pharmacokinetic and scintigraphic assessment, Inter. J. of Pharm. 38 (1987) 221–225.

Communications: The Cutoff Size for Gastric Emptying of Dosage Forms, J. of Pharm. Sciences, vol. 82, No. 8, Aug. 1993, p. 854.

Abstract—Gastric retention system for controlled drug release—having a noncontinuous compressible element which in expanded form resists gastric transit (89–358323/49) May 29, 1989.

Abstract—Carrier for controlled release of drugs in the gastrointestinal tract—consists of a band–shaped, foil=type substrate with holes and which can be charged with active ingredient (96–031024/04) Dec. 14, 1995.

Abstract—Drug delivery device for controlled retention in stomach—comprise erodable polymer shaped to resist passage into intestine to predetermined time (86–306890/47) Oct. 05, 1985.

Abstract—Gastric retention devices, esp. for drug delivery—made from combination of elastic and erodable materials (91–067215/10) Jun. 03, 1991.

PROLONGED RELEASE ACTIVE AGENT DOSAGE FORM ADAPTED FOR GASTRIC RETENTION

This application claims the priority of provisional application Ser. No. 60/055,475, filed Aug. 11, 1997, which is incorporated herein by reference.

FIELD OF THE INVENTION

The present invention is related to the prolonged release of an active agent from a dosage form. More particularly, it relates to a an active agent dosage form adapted for retention in the stomach for a sustained period for delivering the active agent to a fluid environment of use.

BACKGROUND OF THE INVENTION

Controlled release dosage forms that provide for prolonged delivery of active agent formulations to the environment of use have found application for increasing numbers of active agents. However, with respect to pharmaceutical and veterinary active agent formulations, there has been a need not only to provide for prolonged delivery of the active agent over time, but also to provide prolonged delivery of the active agent at a particular location or locations in the environment of use, such as in the stomach.

Certain active agents are absorbed primarily from the small intestine. Generally, the time of passage of different particles through the small intestine does not vary significantly, and passage is generally independent of food intake and particle size. Thus, active agent dissolved in liquid, solid active agent dispersed in liquid and relatively larger delivery units of active agent, such as microcapsules and the like, will traverse the length of the small intestine in substantially the same time frame, usually about 3–5 hours. For active agents that are not easily absorbed by the small intestine or that do not dissolve readily, the window for active agent absorption in the small intestine may be too short to provide a desired therapeutic effect. This fact often creates a need for frequent dosing of active agent in order to provide and maintain adequate levels of active agent in blood plasma. The need for frequent dosing presents compliance problems and is often inconvenient for the user as well.

Since it has been found difficult to alter the transit time of active agent through the small intestine, some emphasis has been placed on attempting to control the transit time of active agents in the stomach. Most active agents are not well absorbed in the stomach, but even in those instances where the active agent is not well absorbed, the continuous release of active agent in the stomach over a prolonged time period will dispense active agent over that same period of time to the small intestine where it can be absorbed. While there is a sound basis for such an approach, physiological characteristics of the stomach and the digestive process have not allowed for much prior success, since the residence time of a particle in the stomach is only mildly dependent of food intake or particle size.

The physiological behavior of the stomach is usually determined by whether it contains food or is empty. Food is mixed and partially digested in the distal stomach (antrum). As the stomach undergoes contractions, partially digested material is discharged into the small intestine and non-digested material is retropelled into the main part of the stomach for further digestion. In the fed state, non-digestible material is not generally able to leave the stomach. At the end of a digestive period, the stomach enters the fasting stage and begins a cycle called the interdigestive myoelectric motor cycle or IMMC.

The IMMC can be considered to be divided into four phases: (1) phase 1 is an approximately one hour period with no contractions; (2) phase 2 is about a forty minute period of intermittent potentials and contractions that increase in intensity over time; (3) phase 3 is a relatively short period, generally between about five to fifteen minutes, of intense contractions (commonly called the "housekeeper wave") that completely empties the stomach; and (4) phase 4 is a short transitory period between the intense activity of phase 3 and the quiescence of phase 1. The different phases move distally from the stomach to the terminal ileum over an approximately two hour period as the cycle is repeated. Since the cycle is interrupted by the receipt of food by the stomach, it is possible to delay the emptying phase, phase 3, by maintaining a fed state. However, it is not practical to regularly maintain the fed state over a long period of time. Consequently, a need exists for a delivery device that can remain in the stomach for a significant period, whether in the fed or fasted state, and deliver active agent to the stomach over a prolonged period of time.

A variety of studies have been conducted in dog and in man to determine sizes of objects that would be retained in the stomach during the fed stage and also in the fasting stage when IMMC is present. Khosla and Davis, *International Journal of Pharmaceutics*, Vol. 62 (1990), pages R9–R11 have reported that a particle size less that 2 mm generally results in emptying from the stomach of the dog. Non-disintegrating tablets having sizes of 7, 11 and 13 mm in diameter were emptied from the human stomach, but the larger sized tablets tended to remain in the stomach longer than the small sized tablets. Tablets larger than 11 mm tended to be emptied only during the IMMC. Davis et al., *Pharmaceutical Research*, Vol. 8, No. 10 (1991) has described retention of radio-telemetry capsules having a size of 25×8 mm in the stomach of human subjects past phase 3 of the IMMC. Timmermans et al., *Journal of Pharmaceutical Sciences*, Vol. 82, No. 8 (1993) has reported the mean resting pyloric diameter in humans as 12.8±7.0 mm. Accordingly, it is important that gastric retentive delivery vehicles are adapted to disintegrate, dissolve or erode to sizes that permit eventual elimination of the vehicle without causing gastric obstruction.

Various attempts to provide active agent delivery devices that remain in the stomach for extended periods or time have been described previously. For example, U.S. Pat. No. 4,851,232 describes a hydrogel reservoir containing tiny pills having a active agent core surrounded by a wall controlling delivery of active agent to the stomach. The hydrogel swells in the stomach to facilitate retention of the active agent reservoir in the stomach over time.

U.S. Pat. No. 4,871,548 describes a dosage form including a mixture of low and high number average molecular weight hydroxypropylmethylcellulose polymers and active agent that swells when in the stomach.

U.S. Pat. No. 4,767,627 describes substantially planar devices formed of bioerodible polymer including active agent that may be compressed and folded for oral administration and then released and unfolded in the stomach, where the devices are to be retained over an extended period of time. The devices have a longest diameter of between 1.6 and 5 cm. It is suggested that as an alternative to incorporating the active agent into the device a controlled release active agent module, mechanically or osmotically driven, can be glued or tethered to the device.

U.S. Pat. No. 5,443,843 describes a plurality of compressible retention arms and an attached controlled release device which in the expanded form resists gastrointestinal transit. The system can have a collar or a belt for receiving and holding a active agent-containing, orally-administrable controlled release device. In a fully expanded configuration for human use, the system is described as having minimum and maximum dimensions of 2.5 and 6.0 centimeters, respectively.

U.S. Pat. No. 5,007,790 describes a sustained release active agent dosage form in the form of a capsule or tablet that includes a plurality of hydrophilic water-swellable, cross-linked polymer particles that swell in the stomach to promote gastric retention and permit gastric fluid to penetrate the particles to dissolve active agent and deliver it to the stomach in the solution state. The particles are indicated to retain their physical integrity over the dosing period. Initially sized particles, indicated to be preferably spherical, are disclosed to be in the range of 50 $\mu$m to 2 mm, swell to a size of about 3 mm. A plurality of particles are packed into a capsule for administration to a patient.

U.S. Pat. No. 5,582,837 describes a dosage form similar to that of U.S. Pat. No. 5,007,790, without the use of a cross-linked hydrophilic polymer. The particles are described as slippery and soft, preferably spherical, and having dimensions on the order of 6 to 18 mm in the swollen state. The particles can be packed into capsules containing 7–25 spherical particles, depending on the size, or formulated into tablets that contain from 2–25 spherical particles.

The use of albumin-cross-linked polyvinylpyrrolidone hydrogels to deliver flavin mononucleotide to dogs has been described by Park et al. in *Journal of Controlled Release*, Vol. 19 (1992) pages 131–134. The hydrogels were maintained in the stomachs of dogs for extended periods, even in the fasted state. Gels with a glassy core tended to remain in the stomach longer than hydrogels without the glassy core. Control of the size of the core was attempted by administration of water in the stomach. While it is possible to control the dimensions of the hydrogel in the dry state, controlling the size of the glassy core within the hydrogel after administration to a subject by addition of water is not suitable for fabrication of a dosage form that can routinely and controllably be retained in the stomach of a subject over a prolonged period of time.

While it is important that the delivery device be adapted to remain in the stomach for a prolonged period, it is also important that the device deliver active agent in a controlled manner. Delivery systems, such as those described below, are representative of the many different systems have been suggested for such controlled delivery of active agents over a prolonged period of time.

For example, U.S. Pat. No. 4,290,426 to Lusted et al describes a cylindrical dispenser for releasing a beneficial agent into a fluid environment at a rate that is governed by the fluid induced relaxation of a polymeric agent contained within the dispenser. The cylindrical dispenser includes an impermeable container that has within it a reservoir and a passageway from the reservoir to the exterior of the container. The reservoir contains a polymer and a beneficial agent. The polymer imbibes fluid from the environment and thereby undergoes relaxation, releasing the beneficial agent from the device. The amount of agent released is dependent on the rate of relaxation of the polymer over time.

Coated dosage forms have also been suggested for delivery of a controlled amount of a beneficial agent over a prolonged period of time. U.S. Pat. No. 5,256,440 describes a process for producing a film coated dosage form. A continuous groove is inscribed in a dosage form core. A latex film is coated onto the core, the groove defining a fixed zone and a detachable zone for the film. The detachable portion of the latex film detaches when it is exposed to the environment of use, thereby exposing a discrete portion of the dosage form core surface. The remainder of the film remains attached to the dosage form core. The exposed portion of the dosage form surface erodes and releases active agent to the environment of use.

Coated tablets for constant and prolonged active agent release are described by Conte et al in *J. Controlled Release*, Vol. 26, (1993) pages 39–47. These GEOMATRIX™ Systems are swellable matrices that are coated or tableted with polymeric barrier layers. Release performances of the systems are modulated as a result of the reduction of the releasing surface exposed to the dissolution medium by the polymeric barrier layer coatings. As the extent of coating of the system's surface is increased, the release kinetics of the system shift toward constant release. These systems are further described in U.S. Pat. No. 4,839,177 to Colombo et al.

U.S. Pat. No. 5,534,263, which is incorporated herein by reference, describes a dosage form useful for the prolonged delivery of an active agent formulation in the form of a matrix having two or more insoluble bands on the surface of the matrix. The exposed surfaces of the matrix erode in a manner that creates additional surface areas to provide for prolonged release of an active agent formulation with determined release profiles.

Additional oral, controlled-release dosage forms include elementary osmotic pumps, such as those described in U.S. Pat. No. 3,845,770, mini-osmotic pumps such as those described in U.S. Pat. Nos. 3,995,631, 4,034,756 and 4,111,202, and multi-chamber osmotic systems referred to as push-pull, push-melt and push-stick osmotic pumps, such as those described in U.S. Pat. Nos. 4,320,759, 4,327,725, 4,449,983, 4,765,989 and 4,940,465, all of which are incorporated herein by reference.

Administration of acyclovir by sipped solution over a four-hour period has been described in *Br. J. clin. Pharmac.*, 21, 459–462 (1986) to achieve an increased contact time with the human stomach and the gastrointestinal tract. The total amount of acyclovir absorbed was increased over that observed with administration of acyclovir tablets. The influence of food on gastric retention time and the absorption of acyclovir has been reported in *International Journal of Pharmaceutics*, Vol. 38 (1987), pages 221–225. As reported there, compared to a lighter meal, the heavier meal slowed the rate of gastric emptying, prolonged small intestinal transit time and decreased absorption of the active agent.

SUMMARY OF THE INVENTION

As can be observed in the above-referenced patents and publications, devices have been described that provide for prolonged delivery of an active agent and retention in the gastric environment. However, there remains a continuing need for improved systems for delivering an active agent to the gastric environment over a prolonged period of time and in a reliable, controllable and reproducible manner. In particular, there is a need for sustained delivery devices that are to remain in the stomach, even during a fasting state in which IMMC is present, for a prolonged period, for example from about 4 hours to up to about 20–24 hours. Such devices should exhibit a combination of flexibility and rigidity so as not to be expelled from the stomach into the pyloric sphincter under fed or fasting conditions, and deliver active agent in a reproducible, controlled manner, over a prolonged period of time.

Accordingly, the present invention is directed to a dispensing device that will provide increased retention time of the device in the stomach over conventional dosage forms and release an active agent formulation in a reliably controllable manner, and further that is easy and inexpensive to manufacture.

In one aspect, the invention is directed to an active agent dosage form for the prolonged delivery of an active agent to the stomach of a human or other animal. The dosage form includes an active agent and a polymer matrix formed of a mixture of a swellable, water soluble polymer that expands when in contact with fluids in the gastric environment and a hydroattractant, preferably water insoluble. The matrix is formed with a rigid or semi-rigid segment in which swelling of the hydrogel is constrained to provide a rigid or semi-rigid section in the dosage form that facilitates the dosage form remaining in the stomach of a subject over a prolonged period of time. In one embodiment, the rigid or semi-rigid section of the dosage form comprises one or more insoluble materials, typically exhibiting low water impermeability and formed as a band circumscribing a portion of the surface of the matrix, that along with the banded portion of the polymer matrix forms the rigid or semi-rigid segment of the dosage form.

The aforementioned insoluble material or band (or bands, if more than one band is utilized) prolongs the period of time in which the polymer matrix retains its integrity in an expanded state and increases the residence time of the dosage form in the stomach. The band limits the transport of fluid into the portion of the polymer matrix which it surrounds and provides the polymer matrix with enough rigidity to permit the dosage form to resist the compressive force of the contractions of the stomach during the housekeeping phase and remain in the stomach for a significantly prolonged period. As the dosage form erodes in the stomach or as active agent diffuses from the matrix, active agent will be released and either absorbed by the stomach or passed from the stomach to the small intestine where it can be absorbed.

In still another aspect, the active agent dosage form comprises (a) a therapeutically-effective amount of an active agent, (b) a polymer matrix in which the active agent is dissolved or dispersed, the polymer matrix including a high molecular weight, water-soluble polymer and a hydroattractant such as a water-insoluble polymer, and, optionally, non-polymeric water-soluble excipients and polymers of molecular weight of less than 10,000 grams per mole, the polymer matrix having an outer surface for exposure to the environment of use, and (c) a band of insoluble material circumscribing a portion of the outer surface of the polymer matrix.

Examples of water soluble polymers are sodium and calcium polyacrylic acid, polyacrylic acid, polymethacrylic acid, polymethylvinylether co-maleic anhydride, polyvinylpyrrolidone, polyethylene oxide, hydroxypropyl cellulose, hydroxypropyl methyl cellulose, hydroxyethyl cellulose, hydroxymethyl methacrylate, sodium carboxymethyl cellulose, calcium carboxymethyl cellulose, methyl cellulose, maltodextrin, xanthan gum, tragacanth gum, agar, gellan gum, kayara gum, alginic acids, pectins, pregelatinized starch, and polyvinyl alcohol, and blends of those polymers. Particularly useful polymer blends are those which form association polymers in the low pH environment of the stomach, such as mixtures of polyacrylic acid and polyethylene oxide or mixtures of polyacrylic acid and polyvinylpyrrolidone.

Examples of hydroattractants are water insoluble polymers such as low substituted hydroxypropyl cellulose, ion exchange resins, microcrystalline cellulose, cross-linked sodium or calcium carboxymethyl cellulose, cellulose fiber, cross-linked polyvinyl pyrrolidone, cross-linked polyacrylic acid, cross-linked Amberlite resin, alginates, chitin, colloidal magnesium-aluminum silicate, corn starch granules, wheat starch granules, rice starch granules, potato starch granules, zein, soya polysaccharide, and sodium carboxymethyl starch, and blends of these hydroattractants.

Examples of non-polymeric water soluble excipients include sugars, such as mannitol, sorbitol, sucrose, lactose, fructose, maltose; salts such as sodium chloride, potassium chloride, calcium sulfate; the ammino acids alanine, arginine, asparagine, aspartic acid, cysteine, glutamic acid, glutamine, glycine, histidine, isoleucine, leucine, lysine, methionine, phenylalanine, proline, serine, threonine, tryptophan, tryosine, and valine; buffering agents such as citric acid, sodium citrate, potassium citrate, succinic acid, fumaric acid, sodium acetate, sodium phosphate monobasic, tartaric acid, sodium potassium tartrate; surface active agents such as poloxamers, polysorbates, lecithin and the like; and effervescing couples such as citric acid blended with sodium bicarbonate, and similar blends. Malodextrin, having a molecular weight of about 400 to 4000 grams per mole, and polymers having similar properties are example of a low molecular weight polymeric materials useful in this invention.

In another aspect, the invention comprises an active agent dosage form adapted to deliver in the stomach, as a single dose and over a prolonged time period, a therapeutically effective amount of the active agent with the relative absorption index of the active agent over the time period being at least 0.5. Preferably, the amount of active agent delivered over the prolonged period by the present invention will be at least 50%, and most preferably at least 80%, of the amount of active agent deliverable in an immediate release, multiple dose regimen over the time period.

In still another aspect, the invention comprises an active agent dosage form adapted for gastric retention over a prolonged period comprising a polymer matrix formed of a water soluble, high molecular weight polymer and a hydroattractant in which the weight percent of the water soluble, high molecular weight polymer is about 10 to 50 weight percent and the weight percent of the hydroattractant is about 5 to 70 weight percent.

In a further aspect of the invention, the invention comprises a composition comprising about 5 weight percent to about 50 weight percent of a polyethylene oxide polymer having a number average molecular weight of between about 100,000 and 9 million grams per mole and about 5 weight percent to about 70 weight percent of a hydroxypropyl cellulose polymer having a hydroxypropyl content of between about 10 weight percent to about 13 weight percent of the hydroxypropyl cellulose polymer.

In another aspect of the invention, the dosage form is formed as a swellable polymer matrix attached to a separate active agent reservoir, from which the active agent is delivered, such as an osmotically-driven active agent reservoir. The polymer matrix is formed as a tube or annular ring and placed about the reservoir, such that swelling of the polymer retains the active agent reservoir within the tube or ring and provides size and gel properties to the dosage form that promotes retention in the stomach over a prolonged period of time. The polymer tube or annular ring is optionally formed with split ends such that upon swelling the ends of the polymer matrix can flare away from the reservoir to substantially increase the effective swollen size of the dosage form over that exhibited in the dry state. The active agent reservoir contributes to the rigidity of the dosage form, such that along with the gel properties of the polymer matrix, the dosage form is retained in the stomach for a prolonged period of time.

In still another aspect, the invention comprises a gastric-retentive, bioerodible active agent dosage form adapted to deliver a therapeutically-effective amount of an active agent selected from the group of antiviral agents, antifungal agents and antibiotic agents at a controlled rate such that the relative absorption index of the active agent delivered is at least 0.5, and preferably greater than 1.

In a further aspect of the invention, the active agent dosage form comprises a unitary compressed dispersion of a solid active agent in a gel-forming, erodible polymer matrix having a first portion that swells in the stomach while maintaining its physical integrity for a prolonged period of time and a second, non-erodible, non-gel-forming portion for promoting retention of the dosage form in the stomach over a prolonged period of time.

In another aspect, the dosage forms of the invention described above may comprise a gastric-emptying delaying agent, i.e., a substance that increases the retention time of the dosage form in the stomach. The gastric-emptying delaying agent may be combined with the composition containing the active agent for local delivery to the environment of use or it may be coated on the dosage form to provide the desired physiological response to delay onset of the IMMC and facilitate retention of the dosage form in the stomach.

BRIEF DESCRIPTION OF THE DRAWINGS

The figures are not drawn to scale, but are set forth to illustrate various embodiments of the invention. Like numbers refer to like structures.

DETAILED DESCRIPTION OF THE INVENTION

Figure 1A:
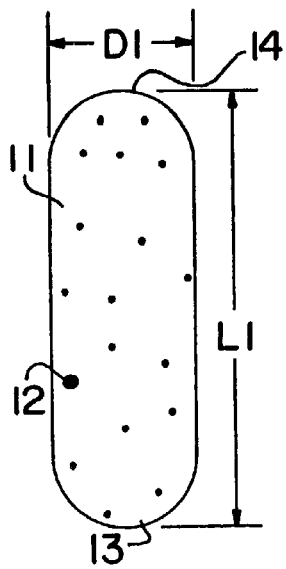
FIGS. 1A and 1B illustrate one embodiment of the delivery device of the present invention, the device in FIG. 1A representing the active agent formulation matrix not including the insoluble material or band and the device in FIG. 1B representing the banded device in prepared form prior to placement in the stomach.

The present invention provides an active agent dosage form that is retained in the stomach for a sustained period of time and that is useful for the prolonged delivery of an active agent formulation to a fluid environment of use. The invention provides for initial and substantially complete delivery of an active agent formulation in the stomach of a user, where the active agent may be absorbed or released from the stomach to be absorbed in the gastrointestinal tract. In particular applications the gastric retentive dosage forms of the invention may allow for less frequent dosing of the active agent than with immediate release formulations or sustained release formulations that are not gastric retentive dosage forms. In other applications the frequency of dosing may be the same, but the gastric retentive dosage forms will beneficially alter the absorption profile of the active agent from that available with immediate release formulations. This may result in increased bioavailability of the active agent or reduced side effects, for example.

Definitions

The phrase "prolonged delivery" or "prolonged period" intends a period of delivery that lasts for several hours to about 24 hours, usually up to about 12 hours, and often between about 4 and 14 hours.

By "insoluble" is intended a material that will not substantially dissolve in the environment of use during the delivery period.

The term "active agent" refers to an agent, drug, compound or other substance, or compositions and mixtures thereof, that provide some pharmacologic, often beneficial, effect. Reference to a specific active agent shall include where appropriate the active agent and its pharmaceutically acceptable salts.

The term "polymer matrix" as used herein means a mixture of a water soluble, high molecular weight polymer and a hydroattractant.

The term "active agent formulation" intends the active agent or the active agent optionally in combination with pharmaceutically acceptable carriers and additional inert ingredients.

The term "active agent formulation matrix", as used herein, comprises the active agent formulation in combination with a polymer matrix, and, optionally, other pharmaceutical excipients.

The terms "adapted for gastric retention" or "gastric retentive" mean, with respect to the dosage form of this invention, that the dosage form will remain in the stomach of a subject for a prolonged period of time.

The terms "rigid" and "semi-rigid" mean, with respect to a portion of the active agent formulation matrix or polymer matrix as defined above, that such portion will not swell and form a gel when initially contacted with gastric fluid.

The term "bioerodible" intends a material that will, at least in part, dissolve, degrade or erode in the fluid environment of use.

The term "bioequivalent" intends, with respect to an active agent dosage form of this invention, that there is greater than a 90% probability that the bioavailability of the active agent as determined by standard methods is 80–125% of the defined dosage form and that there is greater than a 90% probability that the maximum blood plasma concentration and the minimum blood plasma concentration of the active agent as measured by standard methods is 80–125% of the defined dosage form.

The term "polymer" means a material formed from a single polymer or a mixture of polymers.

The term "sustained retention period" means the duration of time equal to or exceeding at least twice the duration of time between the administration of single doses of an active agent that is intended to be administered more than once (e.g., bid, tid, q4h or q5h) over a 24 hour period. For example, if a active agent dosage form is intended for tid dosing (i.e., 3 time a day or every 8 hours), the sustained retention period with respect to such active agent would be a least 16 hours. In the case of a active agent intended for q4h dosing, i.e., every 4 hours, the sustained retention period would be at least 8 hours.

The term "relative absorption index" means the ratio of the amount of active agent delivered over a sustained retention period by a single application of the dosage form of this invention to the amount of active agent delivered by a multiple dose regimen of an immediate release, active agent dosage form over the same sustained retention period, as determined from the area under the blood plasma curve of the subject to which the active agent is administered, wherein the total amount of the active agent contained in the dosage form of the invention is equal to the total amount of active agent contained in the multiple doses of the immediate release, active agent dosage form.

The term "swellable" means, with respect to a polymer or a polymer matrix, that the polymer or polymer matrix is capable of imbibing fluid and expanding when in contact with fluid present in the environment of use.

The terms "therapeutically effective" amount or rate refer to the amount or rate of the active agent needed to effect the desired pharmacologic, often beneficial, result.

The dispensing devices of the invention find use, for example, in humans or other animals. The environment of use is a fluid environment and for the purposes of this invention primarily includes the fluid environment of the stomach and the upper intestinal tract or small intestine. A single dispensing device or several dispensing devices can be administered to a subject during a therapeutic program.

The invention will be better understood with reference to the drawings and the description herein. FIG. 1 depicts one embodiment of the delivery device 10 according to the present invention. The delivery device or active agent dosage form 10 comprises a polymer matrix 11 having active agent 12 (illustrated by the multitude of dots) dissolved or dispersed therein. Polymer matrix 11 typically is formed of combination of a swellable, high molecular weight, water-soluble polymer and a hydroattractant.

Representative examples of the swellable polymer comprising high molecular weight, water-soluble polymers are polyethylene oxide and cellulosic polymer derivatives including hydroxypropyl cellulose, hydroxypropyl methyl cellulose, hydroxyethyl cellulose, sodium carboxy methylcellulose, calcium carboxymethyl cellulose, methyl cellulose, as well as noncellulosics such as maltodextrin, polyvinyl alcohol, polyacrylic acids, alginates, gelatin, natural gums, including guar, lightly crosslinked versions of these polymers, starch graft copolymers and the like. The polymers generally have number average molecular weights over 50,000 grams per mole, such as between 50,000 and 10,000,000 grams per mole and representative viscosities, e.g. for polyethylene oxide in the range of 12–20,000 cps (5% aq, 25° C., MW 100,000–900,000), 400–4000 cps (2% aq, 25° C., MW 1,000,000–2,000,000) and 1500–15,000 cps (1% aq, 25° C., MW 4,000,000–8,000,000) [Brookfield viscometer, rotational spindle]; for methylcellulose in the range of 1,500–18,000 cps (2% aq, 20° C., MW 62,000–134,000) [Ubbelohde tube viscometer]; for hydroxypropyl methylcellulose in the range of 4,000–100,000 cps (2% aq, 20° C., MW 88,000–242,000) [Ubbelohde tube viscometer]; for hydroxyethyl cellulose in the range of 75–400 cps (5% aq, 25° C., MW 90,000–200,000), 400–6500 cps (2% aq, 25° C., MW 300,000–720,000) and 1500–5,000 cps (1% aq, 25° C., MW 1,000,000–1,300,000) [Brookfield viscometer, rotational spindle]; for guar about 5100 cps (1%) [Brookfield viscometer, rotational spindle]; for poly(methyl vinyl ether/maleic anhydride) in the range of 15 to greater than 200 cps (5% aq., MW 20,000–80,000) [Brookfield viscometer, rotational spindle]; for polyvinyl alcohol in the range 27–65 cps (4% aq, 20° C. [Hoeppler falling ball method and 1100–1500 cps (10% aq, 25° C.) [Brookfield viscometer, rotational spindle; for sodium carboxymethyl cellulose in the range of 25–50 cps (2% aq, 25° C.) (MW 90,000) to about 2,500–6,000 cps (1% aq, 25° C.) (MW 700,000) [Brookfield viscometer, rotational spindle]; and for sodium polyacrylic acid 5000–75,000 (0.5% aq) ( MW 750,000–4,000,000) [Brookfield viscometer, rotational spindle]. Polymers having molecular weights between 300,000 and 8,000,000 grams per mole are preferred, and those having molecular weights between about 5,000,000 to 8,000,000 grams per mole are especially preferred. Polyethylene oxide having a number average molecular weight between about 5,000,000 to 8,000,000 grams per mole is most especially preferred, e.g. Polyox 308. Also, especially preferred are methylcellulose type/grade A15C, A18M and hydroxypropyl methylcellulose type/grade K4M, K15M, 100M and F4M (Dow Chemical Company); hydroxyethyl cellulose such as Natrosol® HEC; hydroxypropyl cellulose such as Klucel (Grades H, M, G, J, L, E-Aqualon Company); guar such as Supercol® Guar U (Aqualon Company); pectin such as GENU Pectin (Aqualon Company); carrageenan such as GENU Carrageenan (Aqualon Company); poly(methyl vinyl ether/maleic anhydride) such as Gantrez® AN Copolymer (AN-119, -139, -149, -169, -179, GAF Corporation); polyvinyl alcohol such as Elvanol® 71-30, Elvanol® 85-30, Elvanol® 50-42 and Elvanol® HV (DuPont); sodium carboxymethyl cellulose such as Aqualon cellulose gum grade 7H4; sodium polyacrylic acid such as Carpobol® resin grade 934PNF; and polyacrylic acid such as Carpobol® resin grade 934P.

Representative examples of hydroattractants are water-insoluble polymers such as low substituted hydroxypropyl cellulose, microcrystalline cellulose (Avicel), cross-linked sodium or calcium carboxymethyl cellulose, cellulose fiber (Solka-Floc or Elcema), cross-linked polyvinyl pyrrolidone (Polyplasdone XL), cross-linked Amberlite resin, alginates (Satialgine), colloidal magnesium-aluminum silicate (Veegum), corn starch granules, rice starch granules, potato starch granules, wheat starch granules, sodium carboxymethyl starch (Expotab, Primojel), corn starch/acrylamide/sodium acrylate copolymer, acrylamide/sodium acrylate copolymer and the like. A particularly suitable hydroattractant is hydroxypropyl cellulose having a hydroxypropyl content of between about 8–15 weight percent, and preferably about 10–13 weight percent, such as that supplied as Low Substituted Hydroxypropyl Cellulose grade 11 as manufactured by Shin-Etsu Chemical Company, Ltd., Tokyo, Japan.

Typically, the water soluble, high molecular weight polymer in the polymer matrix is present in from about 5% to about 90% by weight based on the total weight of the active agent formulation matrix, and the hydroattractant is present in from about 5% to about 70% by weight based on the total weight of the active agent formulation matrix. The particular percentages will be chosen to provide the desired retention time in the stomach and the desired release profile of active agent. However, it is presently preferred to have the polymer matrix contain from about 10 weight percent to about 50 weight percent of the water soluble, high molecular weight polymer and from about 10 weight percent to about 60 weight percent of the hydroattractant, with weight percentages of water soluble, high molecular weight polymer in the range of 10 to 40 weight percent and hydroattractant in the range of 25 to 35 being especially preferred.

Figure 1B:
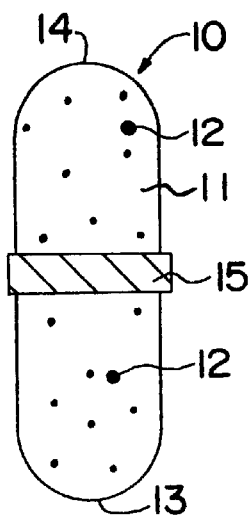

Dosage form 10 is conveniently cylindrically shaped with rounded ends 13 and 14 that facilitate administration of the dosage form in its non-swelled state. In FIG. 1A, the device 10 is shown in preparation prior to application of the insoluble material or band 15 shown in FIG. 1B. The insoluble material exemplified as band 15, circumscribes a portion of the outer surface of the polymer matrix 11. While a single band is illustrated in FIG. 1, additional bands such as illustrated in FIG. 4 can be utilized depending on the particular application for which the device is being used.

The band of insoluble material 15 is applied to the outer surface of the polymer matrix. The insoluble material imparts rigidity to the gel-forming polymer matrix to manage gastric retention time and further control the delivery profile of the active agent of interest. Band 15 typically exhibits low water permeability and will prevent that portion of the polymer matrix which it surrounds from imbibing fluid, thus substantially limiting any swelling of polymer matrix 11 at that location. The number, size, and placement of the insoluble bands that are applied onto the surface of the active agent formulation matrix may be varied to adjust the active agent delivery profile and the retention time in the stomach. For example, bands 0.1 mm to about 12 mm in width, preferably between about 0.5 and 8 mm, may be applied onto the active agent formulation matrix surface. Further, between about 1 and 10 bands may be used, but generally between about 1 and 3 are affixed to the matrix. The bands may be placed close together (i.e., within about 0.5 mm of each other) or may be placed about 8 to 12 mm apart.

Figure 4A:
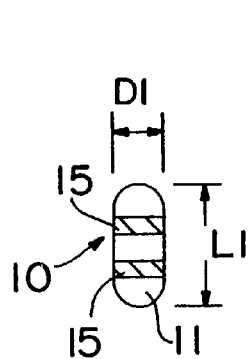
FIGS. 4A–4D illustrate another embodiment of the invention in which two bands of insoluble material have been incorporated on the device illustrated in FIG. 1A.
Figure 4B:
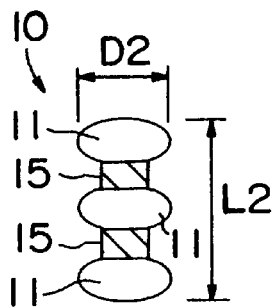
Figure 4C:
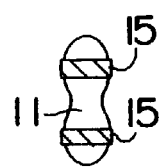
Figure 4D:
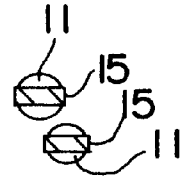

With reference to FIGS. 4A–4D, dosage form 10 is formed with two bands 15, each circumscribing a portion of the surface of polymer matrix 11 in which active agent (not shown) is dispersed. FIG. 4A illustrates dosage form in its initial configuration before it has imbibed any fluid. Upon administration to a subject, dosage form 10 swells as shown in FIG. 4B in those segments of polymer matrix 11 that are not surrounded by bands 15. Because of the low fluid impermeability of bands 15, those portions of polymer matrix 11 surrounded by bands 15 do not appreciably imbibe fluid and the polymer in such segments of the polymer matrix does not swell to any significant extent. FIGS. 4C and 4D illustrate sequential states of dosage form 10 after it is substantially eroded by gastric fluid and contractions of the stomach. Eventually, dosage form 10 will separate into two pieces and be expelled from the stomach.

Figure 5:
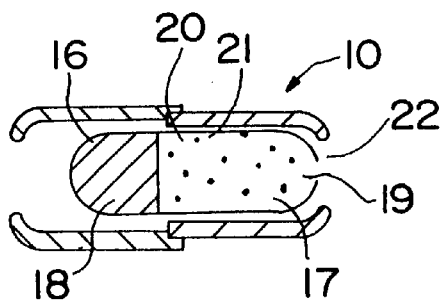
FIG. 5 illustrates another embodiment of the invention that incorporates a swellable polymer matrix tube or ring formed about a separate active agent reservoir for dispensing active agent to the environment of use.
Figure 7:
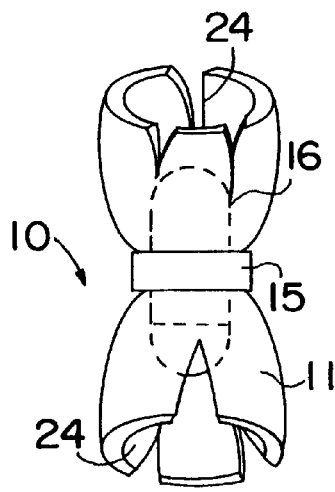
FIG. 7 illustrates still another embodiment of the invention where the polymer matrix tube or ring is formed with split ends which in its swollen state results in the ends of the polymer tube or ring flaring outwardly and swelling to provide a larger effective diameter.
Figure 6:
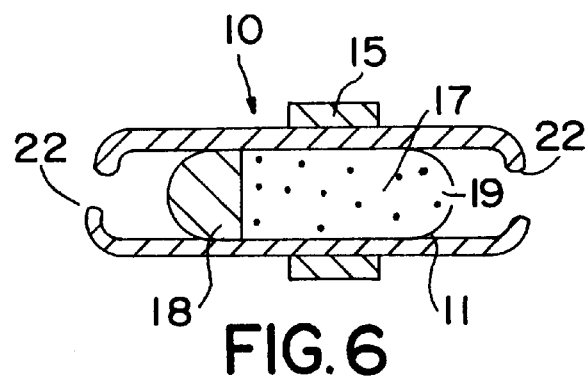
FIG. 6 illustrates an embodiment of the invention that includes a band of insoluble material circumscribing a portion of the device of FIG. 5.

An alternate embodiment of the invention is illustrated in FIGS. 5–7 wherein a separate active agent containing reservoir is utilized with the swellable polymer matrix of the present invention. The swellable polymer matrix 11 is formed in the shape of a tube or annulus, for example by extrusion of the polymer mixture after preparation as described below, and positioned around an active agent reservoir denoted generally as 16. Reservoir 16 will be adapted to deliver active agent to the environment of use over a prolonged period of time when the dosage form is retained in the stomach. In one form it may be an osmotic pump, such as that manufactured by ALZA Corporation, Palo Alto, Calif. as the OROS® active agent dispensers. Various types of osmotic dispensers include elementary osmotic pumps, such as those described in U.S. Pat. No. 3,845,770, mini-osmotic pumps such as those described in U.S. Pat. Nos. 3,995,631, 4,034,756 and 4,111,202, and multi-chamber osmotic systems referred to as push-pull, push-melt and push-stick osmotic pumps, such as those described in U.S. Pat. Nos. 4,320,759, 4,327,725, 4,449,983, 4,765, 989 and 4,940,465, all of which are incorporated herein by reference. In the multi-chamber osmotic systems, the active agent reservoir 16 is typically formed with a active agent compartment 17, containing active agent in the form of a solid, liquid or suspension, as the case may be, and a compartment 18 of a hydrophilic polymer that will imbibe fluid from the stomach, swell and force the active agent from opening 19. Such osmotic pumps are sold commercially and have been described in the patents noted above and other patent and scientific literature. Other active agent delivery systems could be used, but the osmotically-driven systems are preferred for their well controlled delivery of a vast multitude of active agents, including those preferred for delivery by means of and as part of this invention.

Polymer matrix 11 will swell in the stomach and facilitate retention of the active agent reservoir 16 in the stomach during the time that active agent is being delivered. After the polymer has eroded and active agent has been dispensed, the active agent delivery reservoir 16 will pass from the stomach and exit the gastrointestinal tract. With reference to FIG. 5, polymer matrix 11 may be prepared in two parts and joined about the active agent reservoir 16, such as with complementary male ridges 20 and female grooves 21. More simply, it may be prepared in one piece as a tube or annular ring that is fitted or molded about the active agent reservoir 16 as shown in FIG. 6. Additionally, band(s) 15 may be placed about the polymer matrix, limiting the swelling of the polymer matrix in the segment surrounded by the band. Preferably, the tube or ring is formed with split ends 24 as illustrated in FIG. 7, such that upon swelling of the polymer matrix, the ends flare outwardly and create an effective diameter larger than that created in the case where the tube ends are not split. Conveniently, the polymer matrix 11 is injection molded about the active agent reservoir, or alternatively, it may be formed as a tube into which the active agent reservoir is inserted. In certain circumstances, it may be beneficial to have the polymer matrix extend past the end of the active agent reservoir, in which case the tube ends may be crimped to assist in retaining the active agent reservoir within the tube.

However, if a snug fit is provided initially between the inner surface of the polymer tube or annular ring and the outside wall of the active agent reservoir, then the swelling of the polymer matrix normally will be sufficient to retain the tube or annular ring on the active agent reservoir without any additional means being required. Gastric fluid will contact the active agent reservoir and active agent will be dispensed from hole 19 in the reservoir out through holes 22 that are present in the end of the polymer tube 11. While a single hole in the tubular polymer matrix 11 is considered adequate, it is preferred to have a hole at each end of the polymer tube. In another embodiment, illustrated in FIG. 6, the polymer matrix 11 is constrained by a band of insoluble material 15, as has been described elsewhere in this description. Band 15 constrains the polymer matrix and assists in retaining the polymer on active agent reservoir 16. Either alone or in combination with band 15, active agent reservoir 16 provides a rigid segment of the dosage form of the invention that facilitates the dosage form being retained in the stomach for a prolonged period of time. When the polymer matrix has eroded, band 15 will release from the dosage form and be expelled from the stomach and gastrointestinal tract.

The insoluble material comprising band(s) 15 may be any material that is nontoxic, biologically inert, nonallergenic and nonirritating to body tissue, that exhibits little impermeability to liquids, and that maintains its physical and chemical integrity in the environment of use for at least a portion of the dispensing period. The low liquid permeability of the insoluble material serves to limit swelling of the polymer matrix in that section of the polymer matrix that is surrounded by the band.

Insoluble materials from which the bands may be prepared include, for example, polyethylene, polystyrene, ethylene-vinyl acetate copolymers, polycaprolactone and Hytrel® polyester elastomers (Du Pont). Additional banding materials include but are not limited to polysaccharides, cellulosics, cellulose acetate, cellulose acetate propionate, cellulose acetate butyrate, cellulose acetate pseudolatex (such as described in U.S. Pat. No. 5,024,842), cellulose acetate propionate, cellulose acetate butyrate, ethyl cellulose, ethyl cellulose pseudolatex (such as Surelease® as supplied by Colorcon, West Point, Pa. or Aquacoat™ as supplied by FMC Corporation, Philadelphia, Pa.), nitrocellulose, polylactic acid, poly- glycolic acid, polylactide glycolide copolymers, , polycaprolactone, polyvinyl alcohol, polyvinyl acetate, polyethylene vinylacetate, polyethylene teraphthalate, polybutadiene styrene, polyisobutylene, polyisobutylene isoprene copolymer, polyvinyl chloride, polyvinylidene chloride-vinyl chloride copolymer, copolymers of acrylic acid and methacrylic acid esters, copolymers of methylmethacrylate and ethylacrylate, latex of acrylate esters (such as Eudragit® supplied by RöhmPharma, Weiterstadt, Germany), polypropylene, copolymers of propylene oxide and ethylene oxide, propylene oxide ethylene oxide block copolymers, ethylenevinyl alcohol copolymer, poly sulfone, ethylene vinylalcohol copolymer, polyxylylenes, polyamides, rubbers, such as styrenebutadiene, polyisobutylene and the like, natural and synthetic waxes, paraffin, carnauba wax, petroleum wax, white or yellow bees wax, castor wax, candelilla wax, rice bran wax, microcrystalline wax, stearyl alcohol, cetyl alcohol, bleached shellac, esterified shellac, chitin, chitosan, silicas, polyalkoxysilanes, polydimethyl siloxane, polyethylene glycol-silicone elastomers, crosslinked gelatin, zein, electromagnetic irradiation crosslinked acrylics, silicones, or polyesters, thermally crosslinked acrylics, silicones, or polyesters, butadiene-styrene rubber, glycerol ester of partially dimerized rosin, glycerol ester of partially hydrogenated wood rosin, glycerol ester of tall oil rosin, glycerol ester of wood rosin, pentaerythritol ester of partially hydrogenated wood rosin, pentaerythritol ester of wood rosin, natural or synthetic terpene resin and blends of the above.

The banding materials often are also formulated with plasticizers, and optionally with wetting agents, surfactants, opacifiers, colorants, flavorants, taste-masking agents, and the like. Examples of typical plasticizers are as follows: polyhydric alcohols, polyethylene glycol, glycerol, propylene glycol, acetate esters, glycerol triacetate, triethyl citrate, acetyl triethyl citrate, glycerides, acetylated monoglycerides, oils, mineral oil, castor oil and the like.

Figure 2:
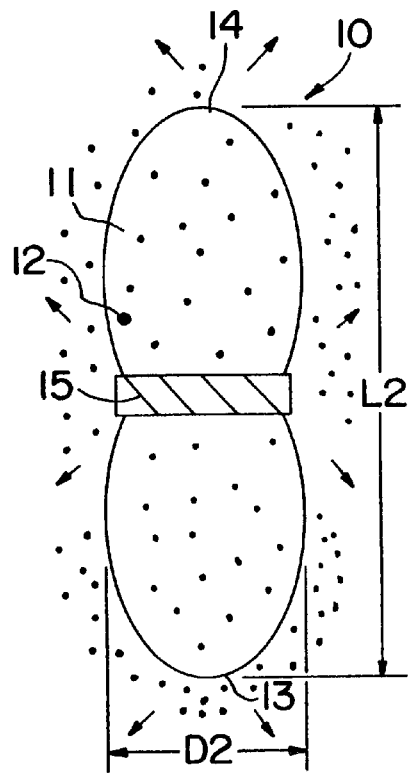
FIG. 2 illustrates the device of FIG. 1B in its initially-swollen state after having expanded in the stomach.

Referring again to the embodiment of the invention depicted in FIG. 1A, the polymer matrix 11 in its non-swelled state has a length L1 and a maximum diameter D1 intermediate the ends 13 and 14. FIG. 2 shows dispensing device 10 after having been placed in the stomach. The active agent formulation matrix 11 on each side of the band 15 has swelled from imbibing fluid from the stomach and begun to erode, thereby releasing active agent 12 to the stomach environment. In contrast to the exposed segments of the swollen polymer matrix 11, band 15 and the portion of the polymer matrix beneath it have not swelled to such an extent. Accordingly, that segment of the polymer matrix surrounded by band 15 is maintained in a constrained and more compressed, non-swollen state than the unbanded portion of the matrix. Since band 15 does not take up an appreciable amount of fluid from the stomach and swell, band 15 retains its substantially rigid or semi-rigid form, and provides an element of rigidity to the dosage form as a whole. While it is not entirely clear how band 15 and the constrained segment of polymer matrix 11 facilitate retention of the dosage form in the stomach through housekeeping waves, it is thought that the band reduces the rate of erosion of the polymer matrix, thus maintaining a larger effective size of the dosage form and reducing the chance for its expulsion from the stomach, for a longer period of time than would otherwise occur if the band was not present. Additionally, the presence of the band on the polymer matrix provides a semi-rigid segment of the dosage form that appears to cause the dosage form to be retropelled into the main area of the stomach as a reaction to the stomach contractions rather than being expelled by the housekeeping wave, as a less rigid gel would be inclined to be.

After swelling, the dosage form 10 has a length L2 and a maximum diameter D2 measured at the widest part of the swollen polymer matrix. Generally, for human applications the largest dimension of the device in the swollen state equivalent to the diameter D2 should be greater than 7 mm, preferably 10 mm or greater, and most preferably 13 mm or greater during the period of residence in the stomach when active agent is being dispensed. Since the active agent formulation is intended to remain in the stomach for a sustained retention period, the effective diameter of the active agent dosage form in when in its swollen state in the stomach may have to be significantly larger than 13 mm, and may extend to more that 50 mm or greater. Larger dosage forms may be appropriate particularly when the polymer matrix is designed to erode relatively rapidly over time in order to provide the required delivery of active agent for therapeutic effect. For applications in animals other than humans, for example in dogs, the maximum diameter should be greater than about 2 mm. The maximum dimension for any particular dosage form will depend on the particular application and animal in which the device is being used.

Such dimensions can be determined by those skilled in the art in accordance with the teaching herein and the various patents and publications noted herein and existing in the related art. A practical consideration, particularly for oral administration to humans, is that the initial size of the device be such that it can be reasonably, comfortably swallowed. For human oral applications, a preferred size of the device in its form prior to administration to the stomach would be on the order of a size 000 capsule to a size 5 capsule. However, it is understood that smaller or larger sizes could be used for particular applications where necessary. Since the dosage forms of the invention may be gel-forming, it may be desirable to wet the outer surface of the dosage form immediately prior to the subject swallowing the dosage form in order to provide a more slippery outer surface and promote ease of swallowing. Alternatively, the matrix core can be inserted into a hard gelatin capsule prior to application of the band in order to facilitate swallowing and also promote ease of manufacture in applying and forming the bands. Upon entering the stomach, that portion of the hard gelatin capsule that is not covered by the band will dissolve, exposing the polymer matrix to fluid in the stomach. As the polymer matrix imbibes fluid, the dosage form will swell in the exposed segments as previously described. The dosage form typically is prepared to allow for swelling at a controlled rate, particularly at a limited initial rate, so that the dosage form does not swell inordinately during the swallowing process and result in obstruction of the esophagus.

It is preferred that the dosage forms of this invention on be administered when the subject is in the fed state to allow time for maximum swelling of the polymer matrix prior to the housekeeping wave being initiated. Generally a meal size that results in a delay of the housekeeping wave of from about 1 to 3 hours is satisfactory. It may be preferable to administer one or more of the dosage forms at the start of each dosing period, depending on the size of the dosage form, to facilitate swallowing and yet provide sufficient dose of active agent. Particularly in those instances where the dosage form is near the lower end of the size range, i.e., the maximum diameter along the longitudinal axis is on the order of 7–13 mm, it is preferable that the dosage form be administered to the subject in the fed state to allow for significant swelling of the dosage form prior to the housekeeping wave occurring. Typically, administration will occur with the meal or within two hours thereafter, and preferably within one hour of completion of the meal. Depending on the half-life of an active agent, once-a-day dosing could conveniently occur with or after dinner. For b.i.d. (i.e., twice-a-day) dosing to a human subject, the dosage form can conveniently be administered with or after breakfast and dinner, but, if after, preferably within one or two hours after conclusion of the meal. For more frequent administration, such as t.i.d., the dosage form may be administered after breakfast, lunch and dinner. For administration within usual meal patterns, it is desirable that the subject consume small amounts of food or liquids prior to administration of the dosage form. The dosage form may be administered prior to the taking of food if administered with a sufficient quantity of liquid so as to delay onset of the housekeeping wave, until consumption of food is initiated.

To facilitate retention of the dosage forms of the invention, particularly if the dosage form is to be administered to a subject in the fasted state, it may be desirable to combine one or more gastric-emptying delaying agents with the active agent composition or coat the dosage form with a composition containing a gastric-emptying delaying agent, i.e., a substance that delays onset of the housekeeping wave of the IMMC. Examples of agents for delaying onset of the housekeeping wave, preferably locally delivered by the dosage form in amounts not resulting in any substantial systemic effect to the subject, as for example, anticholenergic agents such as propantheline, and other agents including, but not limited to, methylcellulose, guar gum, fats such as triglyceride esters, e.g., triethanol myristate, fatty acids of 10–15 carbon atoms, and the like.

Figure 3A:
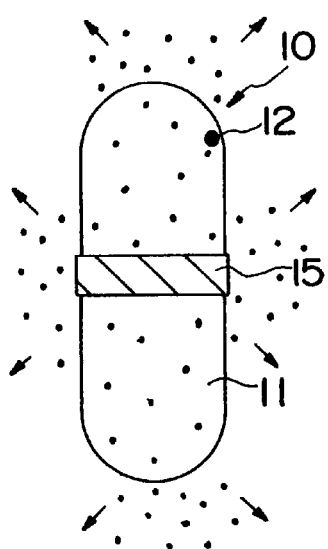
FIGS. 3A and 3B illustrate the device of FIG. 2 at later stages where the device has eroded in the fluid environment of use.
Figure 3B:
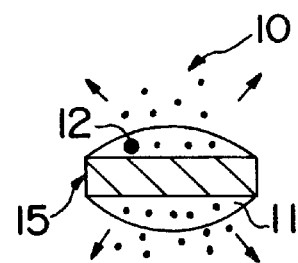

FIGS. 3A and 3B show dosage form 10 after a length of time in the fluid environment of the stomach. Polymer matrix 11 has eroded at the exposed surface of the matrix, i.e., those portions of the matrix not covered by the insoluble material 15 to such an extent that the device 10 is smaller than its initial swollen configuration. Erosion of the matrix will continue to deliver active agent to the stomach until the matrix has substantially eroded so that no significant amount of active agent remains or has eroded to such an extent that the remainder of the dosage form is expelled from the stomach. Band 15 will be expelled from the stomach either alone if it has separated from the dosage form at some time near the end of the delivery period or as part of the remainder of the dosage form expelled from the stomach. In some applications, it may be desirable to form band 15 with weakened portions so that band 15 splits and falls away from the polymer matrix after some predetermined time in the stomach to permit a particular release pattern of active agent from the dosage form over the delivery period.

The polymer matrices useful in this invention can be prepared by standard methods from the materials previously described. Typically, for example, an appropriate quantity of an active agent or agents and the polymer ingredients are separately passed through a screen, such as a screen having a mesh of about 40 wires per inch, to reduce any larger sized materials, and dry mixed. Then, a pharmaceutically-acceptable liquid, having a sufficient vapor pressure to allow subsequent drying over a reasonable period of time, for example 24 hours, is added to the dry mixture and the damp mass is extruded through a mesh screen (e.g. 20 wires per inch) to further mix the materials. Examples of suitable liquids are water, methanol, ethanol, isopropanol, acetone, and the like. After the extrusion process, the mixture is allowed to dry, for example in air overnight at room temperature if the active agent does not require any special handling. After drying, the resulting material is granulated, for example by passing the dried material through a mesh screen (e.g., 20 wires per inch). The granules are combined with a suitable tableting lubricant which has been previously passed through a mesh screen (e.g., 60 wires per inch). The resulting material is tumbled to produce the finished granulation for the tableting process. Tablets are produced using well known methodologies associated with horizontal and vertical compression units using dies and punches of appropriate dimensions. Alternate granulation methods, for example, fluid bed granulation or direct compression granulation can be used as well and such method will be chosen by one skilled in the art depending on the particular nature of the materials being used and the convenience and preference of the fabricator.

While the foregoing process has been described with respect to dry ingredients, including the active agent, methodologies for active agents in other than the solid state can be employed. For example, if the active agent is not crystalline, but is in liquid form, the active agent may first be encapsulated as microcapsules to provide a solid that can be fabricated a described above . Microencapsulation of the liquid active agent can be accomplished by standard encapsulation techniques including, for example, spray coating, spray drying encapsulation, centrifugal suspension, and phase inversion techniques as described in *Polymeric Delivery Systems—Properties and Applications*, ACS Symposium Series 520, edited by El-Nokaly, Piatt and Charpentier (1993), which is incorporated herein by reference. Additionally, liquid active agents can be absorbed into porous clays and polymers and then further incorporated into the polymer matrix of the dosage form.

In order to prepare a device of the present invention, the active agent formulation is first prepared and formed into a matrix of the desired size and shape. The matrix in its initial prepared form is about the size and dimensions of a size "000" to size 5 hard gelatin capsule. The cross-sectional shape of the matrix may be circular or may be oval, triangular, square, hexagonal or other shapes that are easily handled, especially by patients with limited dexterity. Presently preferred shapes are those in which the cross-section is circular or oval. The ring or bands are then placed onto the surface of active agent formulation matrix or printed onto the surface using conventional banding or printing techniques, such as disclosed herein or in U.S. Pat. No. 5,534,263, which is incorporated herein by reference.

As described above, the active agent it self may be in liquid, solid or semisolid form. The active agent formulation may contain additional materials and may be designed in a multitude of ways to provide a specific active agent delivery profile. In one embodiment the active agent is capable of slow dispersion or dissolution in the stomach. In another embodiment, the polymer matrix may contain a surfactant so that the formulation is more readily susceptible to erosion in the stomach. In still another embodiment, the formulation may include a solid surfactant and provide active agent delivery in a finely dispersed form. In yet a further embodiment, the formulation may include coated microspheres of an active agent or microspheres of an active agent and an adjuvant. The active agent either alone or with adjuvant can be delivered simultaneously from the microspheres either by diffusion or by osmosis. Suitable materials useful as active agent carriers and excipients are known in the art and are disclosed in U.S. Pat. Nos. 4,595,583 and 4,874,388, for example. For active agents that may tend to degrade in the stomach, the active agent can be enterically coated to protect the active agent it passes to the small intestine in accordance with conventional coating methods.

The terms "active agent" and "drug" are used interchangeably herein and refer to an agent, active agent, compound, composition of matter or mixture thereof which provides some pharmacologic, often beneficial, effect. This includes foods, food supplements, nutrients, drugs, antiacids, vitamins such as, for example, Vitamin C, microorganism attenuators and other agents that benefit the environment of use. As used herein, the terms include any physiologically or pharmacologically active substance that produces a localized or systemic effect or effects in animals, including warm blooded mammals, humans and primates; domestic household or farm animals such as cats, dogs, sheep, goats, cattle, horses and pigs; laboratory animals such as mice, rats and guinea pigs; zoo and wild animals; and the like. The active agent that can be delivered includes inorganic and organic compounds, including, without limitation, active agents which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system.

Suitable active agents may be selected from, for example, proteins, enzymes, enzyme inhibitors, hormones, polynucleotides, nucleoproteins, polysaccharides, glycoproteins, lipoproteins, peptides, polypeptides, steroids, hypnotics and sedatives, psychic energizers, tranquilizers, anticonvulsants, antidepressants, muscle relaxants, antiparkinson agents, analgesics, immunosuppressants, antiinflammatories, antihistamines, local anesthetics, muscle contractants, antimicrobials, antimalarials, antivirals, antibiotics, antiobesity agents, antidiabetic agents, hormonal agents including contraceptives, sympathomimetics, polypeptides and proteins capable of eliciting physiological effects, diuretics, lipid regulating agents, antiandrogenic agents, antiparasitics, neoplastics, antineoplastics, antihyperglycemics, hypoglycemics, nutritional agents and supplements, growth supplements, fats, ophthalmics, antienteritis agents, electrolytes and diagnostic agents.

Examples of active agents useful in this invention include prochlorperazine edisylate, ferrous sulfate, albuterol, aminocaproic acid, mecamylamine hydrochloride, procainamide hydrochloride, amphetamine sulfate, methamphetamine hydrochloride, benzphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, metformin, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione erythrityl tetranitrate, digoxin, isoflurophate, acetazolamide, nifedipine, methazolamide, bendroflumethiazide, chlorpropamide, glipizide, glyburide, gliclazide, tobutamide, chlorproamide, tolazamide, acetohexamide, troglitazone, orlistat, bupropion, nefazodone, tolazamide, chlormadinone acetate, phenaglycodol, allopurinol, aluminum aspirin, methotrexate, acetyl sulfisoxazole, hydrocortisone, hydrocorticosterone acetate, cortisone acetate, dexamethasone and its derivatives such as betamethasone, triamcinolone, methyltestosterone, 17-β-estradiol, ethinyl estradiol, ethinyl estradiol 3-methyl ether, prednisolone, 17,β-hydroxyprogesterone acetate, 19-nor-progesterone, norgestrel, norethindrone, norethisterone, norethiederone, progesterone, norgesterone, norethynodrel, terfandine, fexofenadine, aspirin, acetaminophen, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, selegiline, chlorpromazine, methyidopa, dihydroxyphenylalanine, calcium gluconate, ketoprofen, ibuprofen, cephalexin, erythromycin, haloperidol, zomepirac, ferrous lactate, vincamine, phenoxybenzamine, diltiazem, milrinone, captropril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captropril, ramipril, enalaprilat, famotidine, nizatidine, sucralfate, etintidine, tetratolol, minoxidil, chlordiazepoxide, diazepam, amitriptyline, and imipramine, and pharmaceutical salts of these active agents. Further examples are proteins and peptides which include, but are not limited to, cyclosporins such as cyclosporine A, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor.

The present invention is particularly useful to deliver active agents that are poorly absorbed in the lower gastrointestinal tract, but well absorbed in the upper gastrointestinal tract (i.e., the small intestine) or active agents that exhibit poor solubility such that the increased retention time in the stomach allows for a greater quantity of active agent to dissolve from the dosage form than would otherwise be dissolved. Typically, antiviral, antifungal and antibiotic agents, e.g. sulfonamides, quinolones, penicillins, cephalosporins, aminoglycosides, and tetracyclines, are representative classes of agents for which the invention is particularly useful. Such antibiotic agents may include, for example, β-lactam antibiotics, vancomycin, clidamycin, erthromycin, trimethoprim-sulfamethoxaazole, rifampin, ciprofloxacin, amoxicillin, clindamycin, ceftriaxone, cefotaxime, chloramphenicol, clindamycin, cefoxitin, doxyclycline, spectinomycin, ofloxacin, rifampin, minocycline, doxycycline, aztreonam, imipenem, meropenem, nitrofurantoin, azithromycin, atovaquone, trimetrexate, dapsone, primaquin, trimetrexate, ketoconazole, floconazole, amphotericin B, itraconazole, trifluridine, foscarnet, zidovudine amantadine, interferon alfa, sulfonamides such as sulfisoxazole, sulfadiazine, and sulfasalazine, quinolones and fluoroquinolones such as, for example, cinoxacin, forfloxacin, diprofloxacin, ofloxacin, spardlosxacin, lomefloxacin, flerexacin, pefloxacin and amifloxacin, gentamicin, tobramycin, amikacin,netilmicin, kanamycin,and neomycin. Representative antiviral agents include acyclovir, famciclovir, foscarnet, ganciclovir, idoxuridine, sorivudine, trifluridine, valacylcovir, vidarabine, didanosine, stavudine, zalcitabine, zidovudine, amantadine, interferons, e.g., interfon alpha, ribavirin, rimantadine, nucleoside RT inhibitors, such as lamivudine and adeforvir, non-nucleoside inhibitors such as nevrapine, delavairidine, Iviride, saquinavir and indinavir, nucleoside DNAp inhibitors such as famciclovir, fialuridine, cidofovir and lobucavir, antisense oligonucleotides such as afovirsen, receptor decoys such as sICAM-1, capsid binding agents such as pirodavir, and neuraminidase inhibitors such as GG167.

Specific examples of active agents that are readily absorbed in the upper gastrointestinal tract relative to the lower gastrointestinal tract are acyclovir, ganciclovir, cimetidine, ranitidine, captopril, methyidopa, selegiline and the like. Specific examples of active agents that exhibit poor solubility in water are diphenidol, meclizine hydrochloride, prochloperazine maleate, phenoxybenzamine, triethylperazine maleate, anisindone, diphenadione erythrityl tetranitrate, digoxin, isofilurophate, acetazolamide, methazolamide, bendroflumethiazide, chlorpropamide, tolazamide, chlormadionone acetate, phenaglycodol, allopurinol, alluminum aspirin, methotrexate, acetyl sulfisoxazole, erythromyciin, progestins, esterogenic, progestational corticosteroids, hydrocortisone, hydrocorticosterone acetate, cortisone acetate, tramcinolone, methyltesterone, 17-beta-estradiol, ethinyl estradiol, prazosin hydrochloride, ethinyl estradiool 3-methyl ether, pednisolone, 17-alpha-hydroxyprogesterone acetate, 19-norprogesterone, norgestrel, norethindrone, progesterone, norgesterone, norethlynodrel, and the like.

Retention of the device of the present invention in the stomach for a prolonged period of time make it especially useful for the localized treatment of gastric acidity and gastrointestinal disorders such as duodenal ulcers, peptic ulcers and chronic gastritis. Representative active agents for such uses include cimetidine, rantitidine, famotidine, nizatidine, zolentine, omeprazole, lansoprazole and active agents useful for the treatment of Helicobacter pylori, such as metronidazole, timidazole, amoxicillin, clarithromycin, minocycline and tetracycline.

The present invention is particularly suited to the administration of active agents against Helicobacter pylori, e.g., antibiotics as exemplified by minocycline, which are able to penetrate the space between the inner stomach lining and the stomach protective mucous layer, where the Helicobacter pylori organism is present, with the result of eradicating the Helicobacter pylori organism either totally or to such a degree that relapse after treatment for a large portion of the treatment population is minimized. The increased residence time of the active agent in the stomach provided by this invention permits an active agent delivery period at the situs of the organism that is longer than that provided by conventional tablets and capsules. The increased efficiency and efficacy of treatment afforded by the present invention allows one to treat gastric disorders in a large number of subjects with dosage forms having a single active agent, preferably minocycline. Accordingly, one avoids the necessity of having to employ complicated treatment regimens directed to the elimination of the Helicobacter pylori organism, such as those that utilize triple drug regimens such as combination of a proton pump inhibitor or a bismuth preparation with two antibiotics.

While for reasons of efficacy, safety, economy, convenience and/or efficiency it may be desirable to utilize a single active agent in the active agent formulation, it is to be understood that more than one active agent may be incorporated into the active agent formulation in a device of this invention, and that the use of the term "agent" or "active agent" in no way excludes the use of two or more such agents or active agents. The agents can be in various forms, such as uncharged molecules, components of molecular complexes or nonirritating, pharmacologically acceptable salts. Also, simple derivatives of the agents (such as ethers, esters, amides, etc) which are easily hydrolyzed by body pH, enzymes, etc, can be employed. Combinations of two or more active agents can optionally be co-delivered, simultaneously or sequentially from the dosage form of this invention. For simultaneous delivery of two or more active agents, the active agents will typically be uniformly dispersed throughout the dosage form. For sequential delivery, different active agents can be selectively placed within the dosage form during its manufacture. For example, a core that contains one active agent can be prepared, and the core coated or formed with an outer layer containing a second active agent. Initially, the agent in the outer portion of the dosage form will be dispensed, and as the dosage form erodes in the stomach, the second active agent will be dispensed at a later time.

The active agent dosage form may include additional ingredients, such as, for example, a buffer or other agents for controlling pH in the stomach or elsewhere in the gastrointestinal tract, an agent or agents for delaying onset of the housekeeping wave, preferably locally delivered by the dosage form in amounts not resulting in any substantial systemic effect to the subject, as for example, anticholenergic agents such as propantheline, and other agents including, but not limited to, methylcellulose, guar gum, fats such as triglyceride esters, e.g., triethanol myristate, fatty acids of 10–15 carbon atoms, and the like, a viscosity regulating vehicle, a surfactant, a dye, a permeation enhancer, a proteinase inhibitor, or other formulation ingredients and additives, as are known in the art. The active agent dosage form may also include minor amounts of low molecular weight polymers which serve useful functions in tablet formation, for example, to improve the tablet cohesiveness after compression or to improve the physical or chemical stability of the dosage form. These polymers are added at quantities less than 10% by weight and preferably less that 5% by weight of the tablet. Examples of such polymers include hydroxypropyl methyl cellulose having molecular weights of less that 20,000 grams per mole, methycellulose having a molecular weight of less than 20,000 grams per mole, polyvinyl pyrrolidone having a molecular weight of less than 50,000 grams per mole, and the like.

The amount of active agent employed in the delivery device will be that amount necessary to deliver a therapeutically effective amount of the agent to achieve the desired therapeutic result. In practice, this will vary widely depending upon the particular agent, the degree of active agent absorption, the severity of the condition, and the desired therapeutic effect. Thus, it is not practical to define a particular range for the therapeutically effective amount of each active agent incorporated into the device. Such ranges can easily be determined by one skilled in the art using conventional methods, for example from dose ranging and plasma level studies. Any references to specific quantities of active agent or specific dose ranges of active agent herein are intended to include the amount or amounts of active agent specified and bioequivalents thereof.

When the delivery device of this invention is being used to substitute for one or more doses of an active agent presented in a conventional dosage form that is usually prescribed for multiple dosing during a predetermined period, the sum of the amounts of active agent present in the multiple doses of the conventional dosage form for use in the period may be used to determine an upper limit on the of the amount of active agent to be included in the device of this invention. For example, if the conventional dosage form contains 200 mg of active agent and is to be administered every 3 hours, a dosage form of this invention may be prepared for administration every 6 hours, and that dosage form may contain 400 mg of active agent which will be delivered over the 6 hour period.

However, when compliance with multiple dosing is a problem, the advantage of administering the dosage forms of the invention at fewer times throughout a twenty-four hour period may provide incentive to incorporate greater amounts of active agent, where such greater amounts do not have any deleterious effects. Also, in certain instances it may be possible and preferable to use less than the sum of the amount of active agent present in the multiple doses in the active agent formulation in the dosage form of the invention where the relative absorption index of the dosage forms of the invention for a particular active agent are high, for example, greater that 1.0. The active agent dosage form of this invention will preferably have a relative absorption index of at least 0.5, more preferably at least 0.8, even more preferably at least 1.0 and most preferably at least 1.2. The specific amount of active agent to be included in the dosage form of the invention can easily be determined by routine dosage studies that compare the blood plasma active agent levels of subjects with conventional dosing and the dosage form of this invention.

The dosage forms of this invention can conveniently release active agent in a controlled and sustained manner over a prolonged period. Typically, active agent will be released from the dosage form at a rate that releases a therapeutically effective amount of active agent to the subject over a substantial portion of the period between administration of the dosage forms. Typically, release will occur over 40% of the period between repeated administration of the dosage form, more preferably at least over 60% of the period, and most preferably over 80% of the period.

In an especially preferred embodiment, the invention comprises a polymer composition having from about 10 weight percent to about 50 weight percent of a water-soluble, high molecular weight polyethylene oxide polymer and from about 10 weight percent to about 60 weight percent of a water-insoluble hydroxypropyl cellulose polymer. The polyethylene oxide polymer has a molecular weight of between about 100,000 and 10,000,000 grams per mole. The hydroxypropyl cellulose polymer preferably has a hydroxypropyl content of between about 8–15 weight percent, and most preferably between about 10–13 weight percent. The composition of this invention is useful to prepare the active agent dosage forms described herein, and finds particular utility with respect to the antiviral, antimicrobial and antifungal active agents described herein.

The following examples are illustrative of the present invention. They are not to be construed as limiting the scope of the invention. Variations and equivalents of these examples will be apparent to those skilled in the art in light of the present disclosure, the drawings and the claims herein.

PREPARATION 1

An example of a active agent which requires frequent dosing is acyclovir. A typical dosing regimen for this antiviral active agent is five doses per day administered every four hours. A dosage form in accordance with this invention for twice daily dosing of acyclovir was formulated according to the following procedures and tested in accordance with the procedures described in Example 1.

Eighteen grams of acyclovir and 3.6 grams of the gel-forming polymer polyethylene oxide, having a number average molecular weight of approximately 8 million grams per mole, were separately screened through a mesh having 40 wires per inch. The polyethylene oxide is supplied under the trade name Polyox® grade 308 as manufactured by Union Carbide Corporation, Danbury, Conn. The sized active agent and polymer were dry mixed. Then, 8.25 grams of a hydroaftractant water-insoluble polymer, hydroxypropyl cellulose having a hydroxypropyl content of 10–13 weight percent and an average fiber particle size of 50 microns, was sieved through the 40-mesh screen and blended into the mixture. The hydroxypropyl cellulose is supplied as Low-Substituted Hydroxypropyl Cellulose grade 11 as manufactured by Shin-Etsu Chemical Company, Ltd., Tokyo, Japan. Anhydrous ethyl alcohol, specially denatured formula 3A, i.e., ethanol enatured with 5 volume percent methanol, was added to the mixture with stirring until a uniformly damp mass formed. This damp mass was extruded with pressure through a screen having 20 wires per inch. The extrudate was then allowed to air dry at room temperature overnight. After drying, the resulting extrudate was passed again through the 20-mesh sieve, forming granules. 0.15 Grams of the tableting lubricant, magnesium stearate, were passed through a sieve having 60 wires per inch. The sized 60-mesh lubricant was then tumbled into the granules to produce the finished granulation.

Portions of the resulting granulation were weighed and compacted with caplet-shaped tooling on a Carver press at pressure head of 1.5 tons. Each tablet weighed approximately 1042 mg and contained approximately 625 mg of the active agent. The shape of the tablet had approximately cylindrical proportions. The diameter was approximately 7.6 millimeters (mm) and the length was approximately 22 mm.

A tube of polyolefin material having an outside diameter of 7.7 mm and having a wall thickness of 0.25 mm was sliced with a razor to produce rings. The width of each ring was approximately 3 mm. One ring was then press fitted onto each caplet such that the ring, or band, was located approximately at the midpoint of the length of the caplet. This step completed the fabrication procedure of the 625 mg acyclovir banded caplet.

EXAMPLE 1

One of the banded devices fabricated in Preparation 1 was placed in a beaker of simulated gastric fluid, as specified in U.S. Pharmacopedia/National Formulary 23/18, having a pH of approximately 1.4 and a maintained temperature of 37° C. After one hour, the device was removed and measured for dimensional change. The length had enlarged to 24 mm and the maximum diameter along the longitudinal axis had enlarged to 10 mm. The swollen device has the general appearance of the dosage form shown in FIG. 2.

Figure 8:
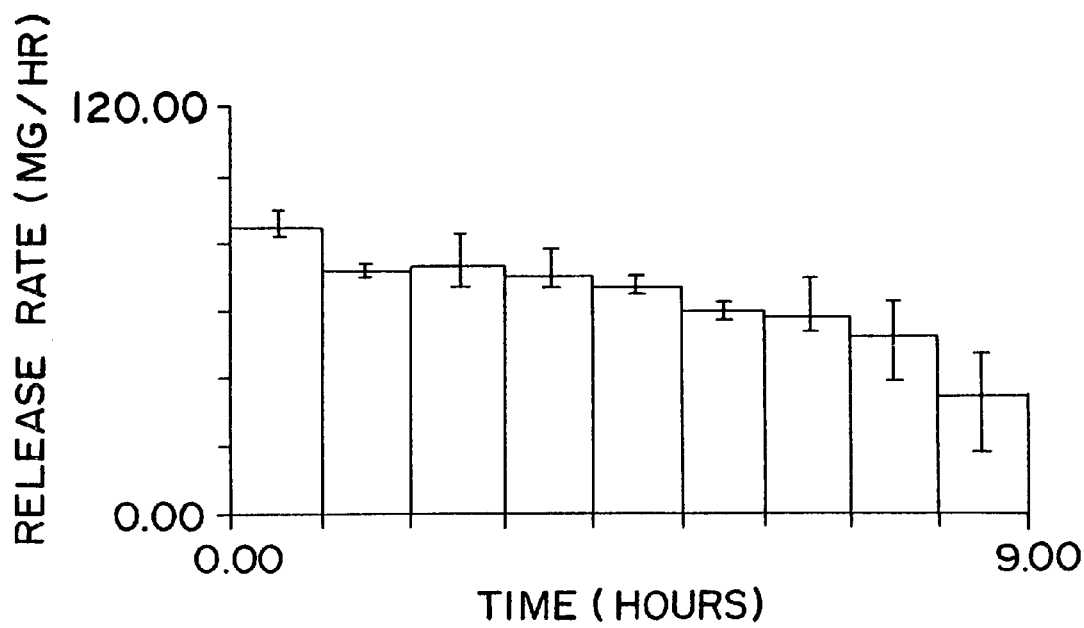
FIG. 8 illustrates a representative in vitro release rate profile for the drug acyclovir from an embodiment of the invention illustrated in FIGS. 1–3.
Figure 9:
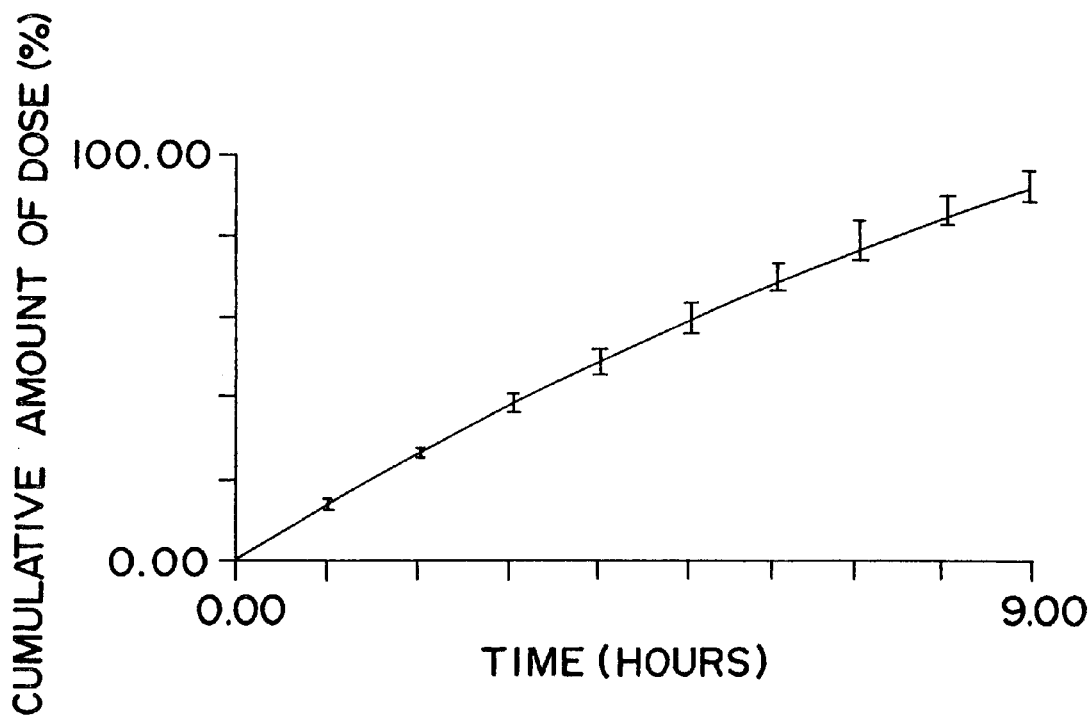
FIG. 9 represents the corresponding cumulative dose of acyclovir released as a function of time from an embodiment of the invention illustrated in FIGS. 1–3.

Five samples of the dosage form from the same manufacturing lot were then tested for release of active agent by shaking at prescribed conditions in an aqueous media simulating the media in the upper gastrointestinal tract. Each dosage form was first placed in a cylindrical, slotted basket having inside diameter of 15 mm and inside length of 52 mm. Each basket had eight slots and each slot was 1–2 mm wide and 52 mm long and positioned lengthwise along the length of the basket. The basket containing the dosage form was then placed in 50 milliliters of simulated gastric fluid and shaken at a frequency of 100 cycles per minutes at an amplitude of 3.7 cm for one hour. Then, the baskets containing the dosage forms were transferred to another set of receptacles having the same fluid media composition and volume as above and shaken for another hour. This procedure was continued until nine 50 ml release receptor samples representing nine hours of release were accumulated. After 9 hours, each basket was transferred to a fresh, single 50 ml receptor where it was then shaken for an additional 3 hours. This completed the testing period. The concentration of active agent in the resulting receptors were then analyzed by using ultraviolet spectrometry assay at a wavelength of 252 nanometers. The release performance data are plotted in FIGS. 8 and 9. Release rate of acyclovir as a function of time is plotted in FIG. 8 and the corresponding cumulative versus time curve is plotted in FIG. 9. The time to deliver 90% of the dose (i.e., "$T_{90}$") of acyclovir was 8.8 hours. It can be observed that the dosage form of this invention releases the antiviral drug acyclovir over a prolonged period of time.

The performance of three dosage forms systems from the same manufacturing lot was then evaluated in animals. Three dogs were fed a standard meal. Then, ½ hour after the meal, one banded caplet as produced above containing 625 mg. of acyclovir was administered orally to each animal. The plasma concentrations of active agent in the animals was monitored during the subsequent 12-hour period. The concentration of active agent was quantitated within the plasma by high pressure liquid chromatography assay. At the completion of this 12-hour test period, the animals were provided a one-week washout period during which time, the level of active agent in the plasma returned to undetectable levels. Then, each animal was administered another course of acyclovir. This second course also consisted of 600 mg of acyclovir but was administered in three divided doses of 200 mg each. These were administered as immediate release doses in gelatin capsules at time zero, 4, and 8 hours. The plasma concentrations were again measured over the 12-hour period following the first dose.

Figure 10:
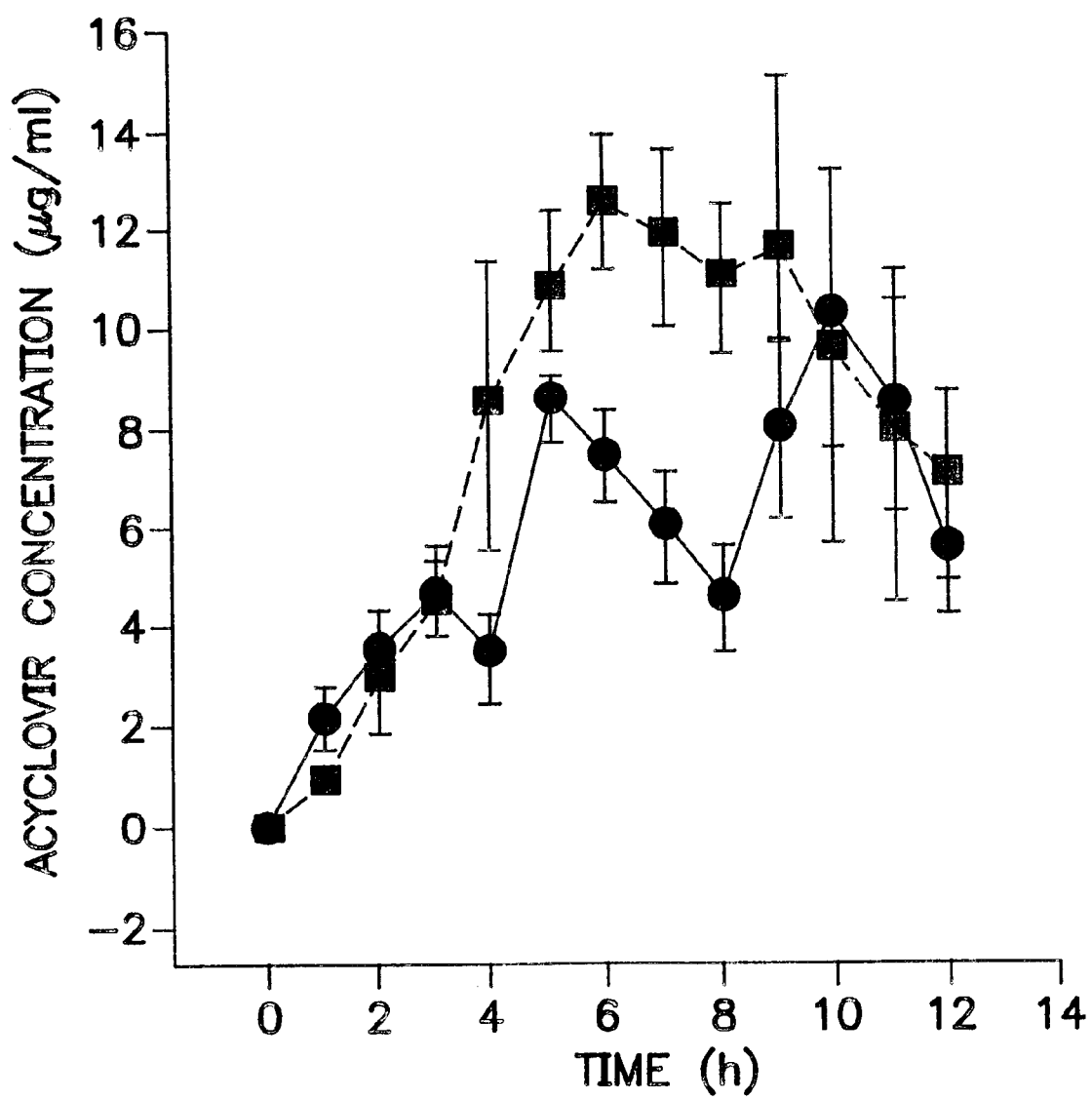
FIG. 10 represents the blood plasma profile in dogs of acyclovir delivered from the embodiment of the invention illustrated in FIGS. 1–3.

Results of the two in vivo studies are shown in FIG. 10. This figure represents active agent plasma concentration as a function of time produced by the dosage form of this invention containing acyclovir compared to the standard capsules of acyclovir. The filled circles represent data from the standard capsules of acyclovir containing the 200 mg of acyclovir, and the filled squares represent data from the dosage forms of the invention containing 625 mg of acyclovir. The continuously increasing plasma profiles through six hours generated by the banded caplet of the invention indicate that is was retained in the upper gastrointestinal tract for approximately 6 hours and active agent was delivered over a sustained retention period. This compares to the immediate-release capsules which show absorption of active agent in the upper tract for only about 1–3 hours. The lack of retention of the active agent as delivered from the capsule form is evidenced by the rapid decay in plasma concentration after each dose from the capsule.

FIG. 10 also illustrates that the single dose of 625 mg of acyclovir as delivered from the caplet of this invention maintained plasma profiles for 12 hours and that the levels were comparable to the 600 mg in divided doses. Moreover, while the total dose delivered from the caplet was equivalent to the total dose delivered from the capsules, the total bioavailability of the active agent, as measured by the area under the plasma/time curves, was significantly higher from the banded caplet than from the capsules; 94 $\mu$g h/ml as compared to 69 $\mu$g h/ml, resulting in a relative absorption index of about 1.36.

EXAMPLE 2

Figure 11:
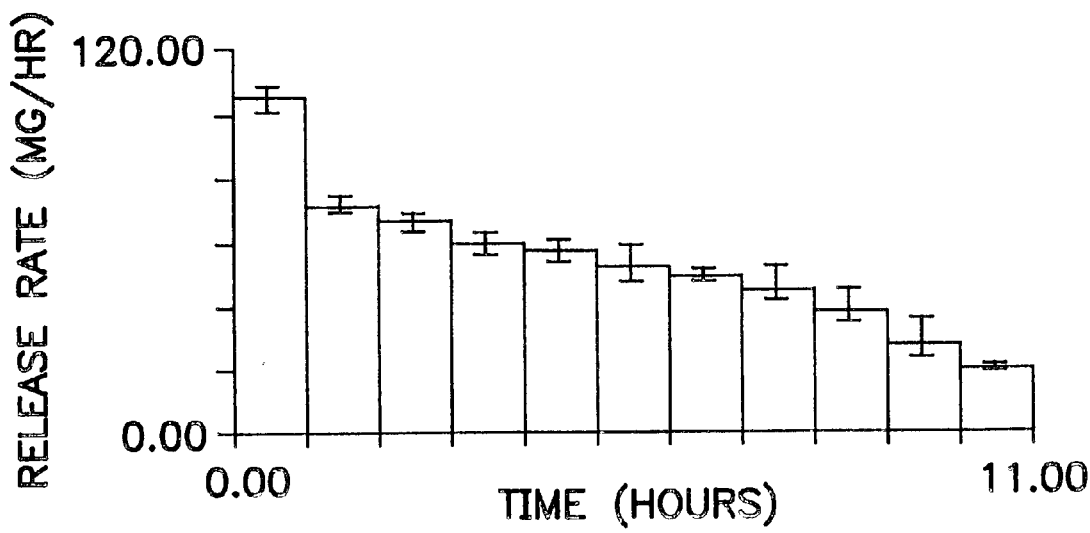
FIG. 11 illustrates a representative in vitro release rate profile for the drug ganciclovir from an embodiment of the invention illustrated in FIGS. 1–3.
Figure 12:
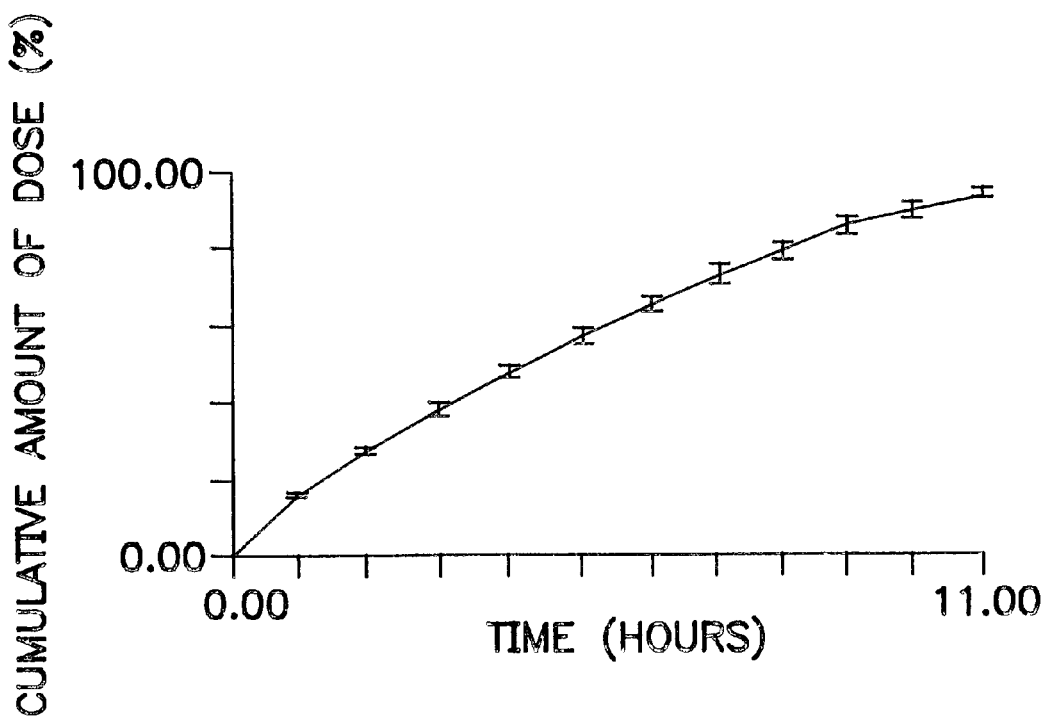
FIG. 12 represents the corresponding cumulative dose of ganciclovir released as a function of time from an embodiment of the invention illustrated in FIGS. 1–3.

Dosage forms of this invention containing 625 mg of the antiviral drug ganciclovir are prepared in accordance with the procedures of Preparation 1. The in vitro release pattern of six ganciclovir dosage forms is illustrated in FIGS. 11 and 12. FIG. 11 represent the release rate versus time and FIG. 12 represents the corresponding cumulative release profile. The time to deliver 90% of the dose was 9.6 hours.

Figure 13:
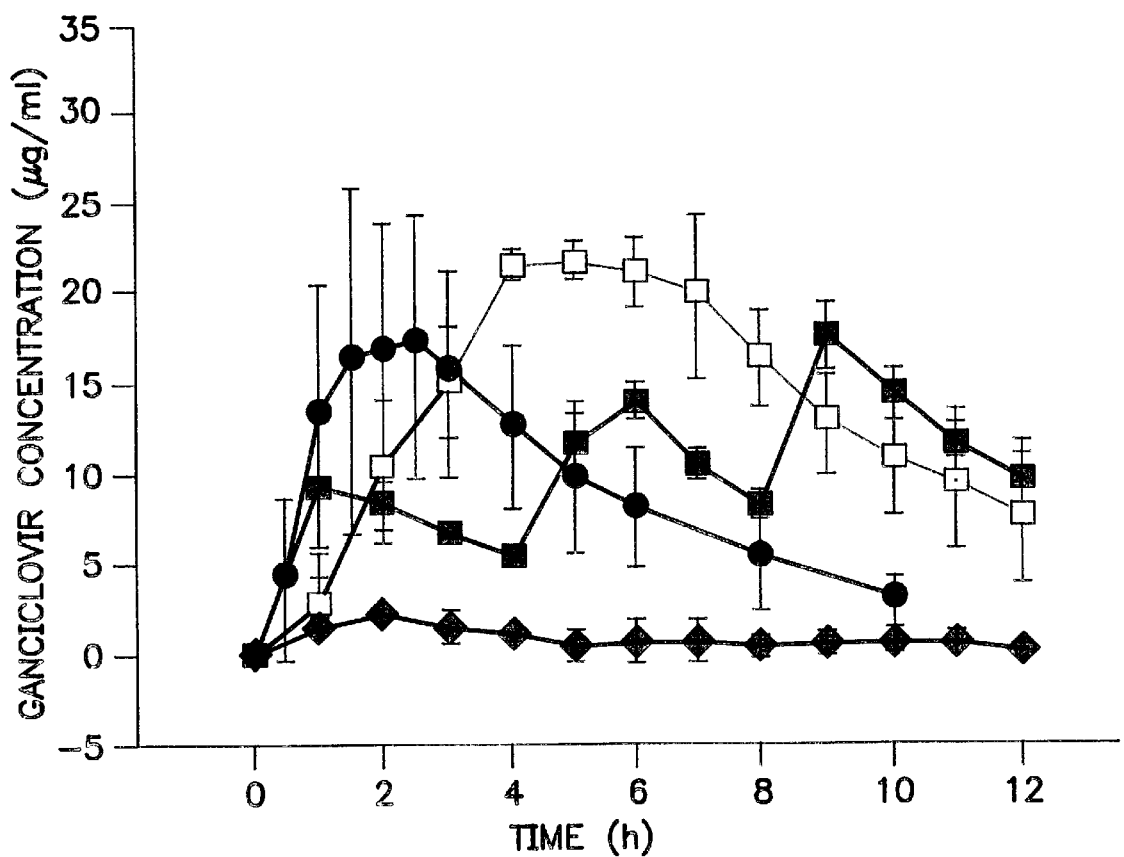
FIG. 13 represents the blood plasma profile in dogs of ganciclovir delivered from the embodiment of the invention illustrated in FIGS. 1–3.

The in vivo performance of three ganciclovir dosage forms of the invention from a single manufacturing lot is represented in FIG. 13. The open square symbols represent average plasma profiles of ganciclovir in three dogs resulting from the administration of the dosage forms as described in Example 1. For comparison purposes, the plasma profile of resulting from the administration of three immediate-release ganciclovir tablets containing 208 mg of drug and administered at 0, 4 and 8 hours, was determined and is shown as the closed square points in FIG. 13. Although the total dose of ganciclovir administered over the time period is substantially equivalent (624 mg for the immediate-release tablets and 625 mg for the dosage form of this invention), the area under the plasma curve for the dosage form of the invention is 157.7 $\mu$g/ml hr as compared to 120.8 $\mu$g/ml hr for the three immediate-release tablets and resulting in a relative absorption index for the dosage forms of the invention of 1.3. In addition to the foregoing comparison, a single immediate-release capsule containing 625 mg of ganciclovir was prepared by filling a gelatin capsule using conventional methods and administered at time zero. The plasma profile of the drug from administration to a dog of that formulation is represented by the closed circular points in FIG. 13. A comparison of the area under the curve of the dosage form of this invention to that of the 625 mg unit dose of ganciclovir results in the dosage form of the present invention having a relative absorption index of 1.69. Moreover, the plasma profiles of ganciclovir delivered by the dosage form of the invention produced elevated levels of the drug in the plasma for a duration of twelve hours, whereas the equivalent dose of the immediate release form produced elevated levels of the drug in the plasma for only about 6 hours. The diamond data points in FIG. 13 indicate that the dosage form of Example 2 was expelled from the stomach of the fasted dog prior to the dosage form swelling to an effective size such that the dosage form would be retained in the stomach, thereby producing only insignificant concentrations of drug in the plasma during the 12-hour test period.

EXAMPLE 3

Equivalent amounts of the following polymers are substituted for the polyethylene oxide in Preparation 1 (all molecular weights are number average molecular weights in grams per mole): hydroxypropyl cellulose (MW: 1,000,000), hydroxypropyl methyl cellulose (MW: 254,000), hydroxyethyl cellulose (MW: 1,300,000), sodium carboxy methylcellulose (MW: 700,000), calcium carboxymethyl cellulose (MW: 700,000), methyl cellulose (MW: 135,000), and polyvinyl alcohol (Elvanol® HV), and dosage forms with a polyethylene band are fabricated to the same dimensions as described in Preparation 1 with equivalent quantities of the active agents acyclovir, ganciclovir and minocycline. The prepared dosage forms are retained in the stomach of a dog for a sustained retention period and deliver the antiviral active agents ganciclovir and acyclovir and the antimicrobial active agent minocycline over a prolonged period of time.

EXAMPLE 4

Dosage forms containing equivalent quantities of the antiviral drugs acyclovir and ganciclovir and the antibiotic minocycline are prepared according to the procedures in Preparation 1, except that the nonwater soluble hydroattractant used is, respectively, microcrystalline cellulose (Avicel), cross-linked sodium or calcium carboxymethyl cellulose, cellulose fiber (Solka-Floc, Elcema), cross-linked polyvinyl pyrrolidone (Polyplasdone XL), cross-linked Amberlite resin, alginates (Satialgine), colloidal magnesium-aluminum silicate (Veegum), corn starch granules, rice starch granules, potato starch granules, and sodium carboxymethyl starch (Expotab, Primojel). The prepared dosage forms are retained in the stomach of a subject and deliver active agent over a prolonged period of time.

EXAMPLE 5

The following active agents are substituted, in the quantities indicated in the parentheses following each active agent listed, for the quantity of acyclovir in Example 1: cimetidine (400 mg; 800 mg, 1200 mg, 1600 mg), ranitidine (150 mg; 200 mg, 300 mg), captopril (12.5 mg; 25 mg; 50 mg; 100 mg, 150 mg), methyldopa (125; 250; 500 mg), and selegiline (5 mg, 10 mg) and the dosage forms are prepared in the same manner as described in Example 1. The prepared dosage forms are retained in the stomach of a subject and deliver active agent over a prolonged period of time.

EXAMPLE 6

Dosage forms of this invention containing 600 mg of acyclovir are fabricated according to the procedures of Preparation 1, except that the tablet is inserted into a size "00" hard gelatin capsule before banding. The band is applied by a printing process using the methods and compositions described in U.S. Pat. No. 5,534,263, incorporated herein by reference, where the band material is ethyl acrylate/methyl methacrylate 70:30 copolymer (Eudragit NE 30 D, Rohm Tech). The resulting dosage form is smooth and easy to swallow.

EXAMPLE 7

A gastric platform dosage form of the antihistamine drug, fexofenadine hydrochloride, was prepared according to the following procedures. 11.5 Grams of the drug, 30 grams of polyethylene oxide, 54 grams of low-substituted hydroxypropyl cellulose, and 3.7 grams of polyvinyl pyrrolidone were individually passed through a sieve having 40 wires per inch, and then the three components were tumble mixed together for 10 minutes. The polyethylene oxide (Polyox® WSR-N-60K as supplied by Union Carbide, Danbury, Conn.) had a molecular weight of approximately 2 million grams per mole, the polyvinyl pyrrolidone (Povidone® K2932 as supplied by GAF Corporation, New York, N.Y.) had a molecular weight of approximately 45,000 grams per mole and the hydroxypropyl cellulose (LHPC-II supplied by Shin-Etsu Chemical Company, Tokyo, Japan) had a hydroxypropyl content of approximately 11 weight percent. Anhydrous ethyl alcohol formula SDA 3A was slowly added to the dry mixture with stirring until a uniform damp mass was formed. The damp mass was forced thorough a sieve with 20 wires per inch, forming elongated granules which were then air dried at ambient room conditions overnight. The resulting dried granules were then passed through the 20 mesh sieve forming more rounded granules. Then, 0.30 grams of the flow-promoting agent, colloidal silicon dioxide (Aerosile® 200 supplied by Degussa Inc, New York, N.Y.), was dry mixed into the blend. Finally, 0.5 grams of the tableting lubricant, magnesium stearate, previously passed through a sieve having 60 wires per inch, was tumble blended into the bulk. This produced the final granulation. Individual portions of the granulation weighing approximately 1042 mg were compressed with size 0 caplet tooling on a Carver press with a force of about 1.5 tons. Each tablet contained the unit dose of 120 mg of fexofenadine hydrochloride.

A solution for use in film coating the tablets was then prepared by stirring 40 grams of methyl cellulose (Methocel A 15 LV Premium supplied by Dow Chemical, Midland Mich.) and 10 grams of sorbitol 950 grams of purified water at room temperature. The mixture was then chilled overnight at 9° centigrade to complete dissolution. The tablets from above were then transferred to a pharmaceutical coating pan spray coated with the solution in a current of warmed air until a dry film coating weight of 37 mg was deposited onto each tablet.

An aqueous dispersion for use in banding the tablets was prepared by dissolving 30 grams of triacetin in 174.75 grams of ethyl acrylate methylmethacrylate 70:30 copolymer aqueous dispersion (Eudragit® NE40D supplied by Rohm Corporation, Darmstadt, West Germany). Then, 0.1 grams of anti-foam agent ( Simethicone Q7-2587, Dow Chemical, Midland, Mich.) was blended into the mixture. This formed the final composition of the banding dispersion.

The film coated tablets from above were then banded by applying a the above banding dispersion in a transfer printing process using a printing wheel having a width of approximately 100 mils (2.54 mm). The freshly banded system was then dried in warm air to remove the water from the aqueous dispersion, leaving a single band located in the center of the cap let having a width of approximately 120 mils (3.05 mm) and a weight of approximately 21 mg. The entire banded system was then overcoated with more of the aqueous-based film coat solution using the formulation and process as described above until a film coat weight of 31 mg was applied. This completed fabrication of the dosage form.

Three of the resulting systems were tested in vitro according to the procedures described in EXAMPLE 1 except the ultraviolet assay wavelength was 260.4 nanometers. The dosage forms demonstrated a mean release rate of 10.9 mg/hr between hourly intervals 1 and 11 in the release rate assay. The $T_{90}$ of the dosage form was approximately 9.8 hours demonstrating that the dosage forms released active agent over a prolonged period of time.

Systems from this batch were then tested in four animals according to the procedures in EXAMPLE 1. The concentration of drug in the plasma as a function of time increased for approximately 6 hours after the initial dosing, demonstrating retention of the dosage forms in the stomach over a prolonged period.

EXAMPLE 8

A gastric platform dosage form delivering the antibiotic, minocylcine, for treatment of Helicobacter pylori gastritis, gastric and duodenal ulcers, was fabricated. The procedures for fabrication were those specified in EXAMPLE 7. 17.8 Grams of minocycline hydrochloride, 24.6 gams of polyethylene oxide 53.8 grams of low-substituted hydroxypropyl cellulose, 3 grams of polyvinyl pyrrolidone 0.3 grams of colloidal silicon dioxide, and 0.5 grams of magnesium stearate were granulated according to the procedures in EXAMPLE 7. The excipients were the same as in this example except the polyethylene oxide had a molecular weight of approximately 4 million grams per mole (Polyox WSR 301). The granulation was compressed into caplets weighing 1042 mg where each tablet contained a unit dose of 185 mg of minocycline hydrochloride. The tablets were film subcoated with a coating weight of 52 mg , banded with a 21 mg band, and overcoated with 21 mg of film. The compositions of the subcoat, band, and overcoat were the same as disclosed in EXAMPLE 7.

The resulting dosage forms were then tested in vitro using the procedures in EXAMPLE 1 except the wavelength for ultraviolet assay was 353.4 nanometers. The dosage forms released drug over a prolonged period and produced a $T_{90}$ value of approximately 10.9 hours. The dosage forms provided a mean release rate of about 18.2 mg/hr determined between hourly intervals 1 and 7 of the release rate assay.

Four systems from the same batch were then evaluated in vivo according to the procedures disclosed above. An ascending plasma concentration over a period of approximately 6 to 8 hours was observed and indicates retention of the dosage forms in the stomach and delivery of drug for a prolonged period after dosing.

The present invention is described and characterized by one or more of the following technical features and/or characteristics, either alone or in combination with one or more of the other features and characteristics: an active agent dosage form adapted for gastric retention that comprises (a) a therapeutically-effective amount of an active agent, (b) a polymer matrix in which the active agent is dissolved or dispersed, the polymer matrix including a high molecular weight, water-soluble polymer and a hydroattractant, preferably water insoluble, the polymer matrix having an outer surface for exposure to the environment of use, (c) a band of insoluble material circumscribing a portion of the surface of the polymer matrix, and optionally a gastric-emptying delaying agent; a number average molecular weight of the water-soluble polymer being between about 100,000 and 20,000,000 grams per mole; the water soluble polymer being polyethylene oxide, hydroxypropyl cellulose, hydroxypropyl methyl cellulose, hydroxyethyl cellulose, sodium carboxy methylcellulose, calcium carboxymethyl cellulose, methyl cellulose, pregelatinized starch, maltodextrin, polyacrylic acid or its sodium or potassium salts, or polyvinyl alcohol; the hydroattractant being low-substituted hydroxypropyl cellulose, microcrystalline cellulose, cross-linked sodium or calcium carboxymethyl cellulose, cellulose fiber, cross-linked polyvinyl pyrrolidone, cross-linked Amberlite resin, alginates, colloidal magnesium-aluminum silicate, cross-linked polyacrylic acid or its sodium or potassium salts, corn starch granules, rice starch granules, potato starch granules, or sodium carboxymethyl starch; a gastric retentive dosage form adapted for delivery of active agents that are relatively insoluble or have a short absorption window in the small intestine, such as where the active agent is an antiviral, antimicrobial or antifungal active agent, and especially where the active agent is acyclovir, ganciclovir, cimetidine, ranitidine, captopril, methyldopa, selegiline, minocycline or fexofenadine or a pharmaceutically acceptable salt thereof; a polymer matrix in which the weight percent of the water soluble polymer in the polymer matrix is about 10 to 90 weight percent and weight percent of the hydroattractant in the polymer matrix is about 5 to 70 weight percent; a dosage form adapted to deliver in the stomach, as a single dose and over a prolonged time period, preferably at least 4 hours, and even more preferably 8–12 hours, a therapeutically-effective amount of an active agent, with the relative absorption index of the dosage form being at least 0.5, and preferably at least 1.0; a unitary compressed dispersion of a solid active agent in a gel-forming, erodible polymer matrix having a first portion that swells in the stomach while maintaining its physical integrity for a prolonged period of time and a second, non-erodible, non-gel-forming portion for promoting retention of the dosage form in the stomach over a prolonged period of time; the water soluble polymer being polyethylene oxide having a number average molecular weight of at least 100,000 grams per mole; a composition comprising about 5 weight percent to about 50 weight percent of a polyethylene oxide polymer having a number average molecular weight of between about 100,000 and 20,000,000 grams per mole and about 5 weight percent to about 60 weight percent of a hydroxypropyl cellulose polymer having a hydroxypropyl content of between about 10 weight percent and about 13 weight percent of the hydroxypropyl cellulose polymer; an active agent dosage form adapted for gastric retention comprising an active agent selected from the group consisting of acyclovir, ganciclovir, metformin, bupropion, orlistat and minocycline, and a bio-erodible polymer, wherein the dosage form releases a therapeutically effective amount of the active agent to the stomach of a subject over at least a 6 hour period; an active agent dosage form adapted for gastric retention comprising an active agent reservoir adapted to deliver active agent over a prolonged period to the stomach of a subject to which the dosage form is administered and a polymer matrix including a high molecular weight, water-soluble polymer and a hydroattractant combined with the active agent reservoir and adapted to expand when contacted with fluid in the stomach of the subject and promote retention of the dosage form in the stomach of the subject; a dosage form wherein the polymer matrix is tubular and surrounds the active agent reservoir comprising a band of insoluble material circumscribing at least a portion of the polymer matrix; delivery of active agent from the active agent reservoir that is osmotically driven; gastric-retentive, bioerodible active agent dosage forms adapted to deliver an active agent at a controlled rate such that the relative absorption index of the active agent delivered is at least 0.5; a gastric-retentive, bioerodible active agent dosage form adapted to deliver a therapeutically effective amount of the active agents acyclovir, ganciclovir, cimetidine, ranitidine, captropil, methyldopa, selegiline, minocycline, metformin, bupropion, orlistat and fexofenadine, or a pharmaceutically acceptable salt thereof, to the stomach of a subject over a sustained retention period and bioequivalents thereof; a method of treating a subject in need thereof with an active agent that comprises administering the active agent to the subject in an active agent dosage form comprising a water soluble, swellable polymer and a hydroattractant adapted for gastric retention and release of the active agent over a prolonged period; a dosage form and method for administering at least 500 mg of acyclovir to a subject over at least a 12 hour period ; a dosage form and method for administering at least 500 mg of ganciclovir to a subject over at least a 12 hour period; a dosage form and method for administering at least 100 mg of minocycline to a patient over at least a 12 hour period; a method of administering a gastric retentive dosage form that is adapted to swell in the stomach of a subject that comprises administering the dosage form to the subject in the fed state.

The above description has been given for ease of understanding only. No unnecessary limitations should be understood therefrom, as modifications will be obvious to those skilled in the art.

What is claimed is:

1. An active agent dosage form adapted for gastric retention comprising (a) a therapeutically-effective amount of an active agent, (b) a polymer matrix in which the active agent is dispersed or dissolved, the polymer matrix including a swellable, water-soluble polymer having a number average molecular weight of between about 100,000 and 20,000,000 grams per mole and a hydroattractant, the polymer matrix having an outer surface for exposure to the environment of use, and (c) at least one band of insoluble material circumscribing a portion of the surface of the polymer matrix.

2. The dosage form of claim 1 comprising a gastric-emptying delaying agent.

3. The active agent dosage form of claim 1 wherein the water soluble polymer is selected from the group consisting of polyethylene oxide, hydroxypropyl cellulose, hydroxypropyl methyl cellulose, hydroxyethyl cellulose, sodium carboxy methylcellulose, calcium carboxymethyl cellulose, methyl cellulose, polyacrylic acid, maltodextrin, pregelatinized starch and polyvinyl alcohol.

4. The active agent dosage form of claim 3 wherein the hydroaftractant is selected from the group consisting of low-substituted hydroxypropyl cellulose, microcrystalline cellulose, cross-linked sodium or calcium carboxymethyl cellulose, cellulose fiber, cross-linked polyvinyl pyrrolidone, cross-linked polyacrylic acid, cross-linked Amberlite resin, alginates, colloidal magnesium-aluminum silicate, corn starch granules, rice starch granules, potato starch granules and sodium carboxymethyl starch.

5. The active agent dosage form of claim 4 wherein the active agent is selected from the group consisting of antiviral, antimicrobial, antidiabetic, antihyperglycemic, hypoglycemic, antidepressant, antiobesity and antifungal active agents.

6. The active agent dosage form of claim 5 wherein the active agent is selected from the group consisting of acyclovir, ganciclovir, cimetidine, ranitidine, captopril, methyldopa, selegiline, minocycline, metformin, bupropion, orlistat, fexofenadine and pharmaceutically acceptable salts thereof.

7. The active agent dosage form of claim 4 wherein the weight percent of the water soluble polymer in the polymer matrix is about 5 to 90 weight percent and weight percent of the hydroattractant in the polymer matrix is about 5 to 60 weight percent.

8. The active agent dosage form of claim 1 wherein the dosage form is adapted to deliver in the stomach, as a single dose and over a prolonged time period, a therapeutically-effective amount of the active agent, the relative absorption index of the dosage form being at least 0.5.

9. The active agent dosage form of claim 8 wherein the prolonged time period is at least 4 hours.

10. The active agent dosage form of claim 9 wherein the time period is between about 8 to 12 hours.

11. The active agent dosage form of claim 8 wherein the relative absorption index is at least 1.0.

12. The dosage form of claim 2 wherein the gastric-emptying delaying agent is selected from the group consisting of anticholonergic agents, methylcellulose, guar gum, fats and fatty acids of 10–15 carbon atoms.

* * * * *